United States Patent [19]

Bartroli et al.

[11] Patent Number: 5,344,839

[45] Date of Patent: Sep. 6, 1994

[54] SULFONAMIDES AS ANTIFUNGAL AGENTS

[75] Inventors: Javier Bartroli; Manuel Anguita; Jordi Belloc; Elena Carceller; Carmen Almansa, all of Barcelona, Spain

[73] Assignee: J. Uriach & Cia. S.A., Barcelona, Spain

[21] Appl. No.: 2,898

[22] Filed: Jan. 11, 1993

Related U.S. Application Data

[60] Division of Ser. No. 945,589, Sep. 16, 1992, which is a continuation-in-part of Ser. No. 772,838, Oct. 8, 1991, abandoned.

[30] Foreign Application Priority Data

Oct. 8, 1990 [ES] Spain ................................ 9002712

[51] Int. Cl.$^5$ .................... A01N 43/76; A61K 31/42; C07D 413/14; C07D 413/06
[52] U.S. Cl. ................................ 514/374; 514/309; 514/312; 546/141; 546/153; 546/157
[58] Field of Search ............... 548/215; 514/374, 309, 514/312; 546/141, 153, 157

[56] References Cited

PUBLICATIONS

Konosu et al., "Triazole Antifungals II, etc.", Chem. Pharm. Bull 38 (9) 2476–2486 (1990).

*Primary Examiner*—Patricia L. Morris
*Attorney, Agent, or Firm*—Rothwell, Figg, Ernst & Kurz

[57] ABSTRACT

The present invention relates to new sulfonamides having the formula I:

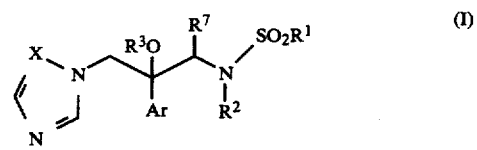

wherein:

$R^1$ represents an alkyl, aryl or heteroaryl group; $R^2$ is hydrogen or an alkyl, aryl or heteroaryl group; or $R^1$ and $R^2$ may form a ring; $R^3$ is hydrogen or may form an oxazolidine ring together with $R^2$, and this ring may be optionally susbtituted by one or two alkyl, aryl or heteroaryl groups at the position 2; $R^7$ is hydrogen or alkyl; X is CH or N; Ar is a phenyl ring or a substituted phenyl ring. The invention also relates to a procedure for their preparation and to pharmaceutical and agrochemical compositions containing them. These compounds are antifungal agents.

11 Claims, No Drawings

SULFONAMIDES AS ANTIFUNGAL AGENTS

This application is a divisional of Ser. No. 07/945,589, filed Sep. 16, 1992, pending which is a continuation-in-part of Ser. No. 07/772,838, filed Oct. 8, 1991, (abandoned).

The present invention relates to a new series of sulfonamides having a patent antifungal activity. The invention also relates to a process for their preparation, to their use in the treatment of fungal infections in humans, animals and plants, and to pharmaceutical and agrochemical compositions containing them.

The compounds of the present invention are antifungal agents whose mechanism of action is based on the inhibition of the biosynthesis of ergosterol in fungi. Other antifungal agents acting in this way are known in the medical practice and are currently used in therapy. Some of them are applied in the topical treatment of fungal infections of the skin, vagina and nails. More recently discovered compounds are used orally in the treatment of systemic and organ micoses, such as candidiasis, aspergillosis, criptoccocal meningitis, coccidioidomycosis, paracoccidio-idomycosis, histoplasmosis and blastomycosis. These diseases appear frequently in immunosupressed patients, such as AIDS and cancer patients. Some other compounds related to the ones of the present invention are also used as agrochemicals to protect plants from a variety of fungi.

Patent EP 97,469 describes certain triazole derivatives of formula

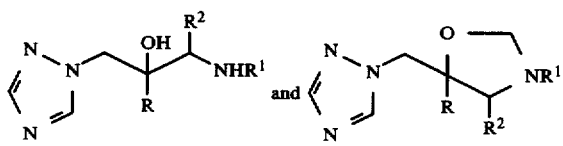

where R is aryl and $R^1$ is a $C(=X)NR^2R^3$ or a $C(=O)R^3$ group, where X is O or S, $R^2$ is H or $C_1-C_4$ alkyl and $R^3$ is H, $C_1-C_4$ alkyl, $C_3-C_6$ cycloalkyl, aryl, aralkyl or heteroaryl, or $R^2$ and $R^3$ together with the nitrogen atom to which they are bound form a 1-pyrrolidine or piperidine cycle, but no mention to $R^1$ being a $SO_2$- group is made.

Patent EP 332,387 discloses certain amides of formula

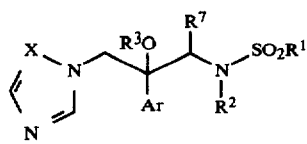

where R is aryl, $R^2$ is $C_1-C_6$ alkyl, and $R^1$ is a $C(=O)R^3$ group, where $R^3$ is alkyl or aryl. Again, no mention to $R^1$ being a $SO_2$- group is made.

The present invention relates to new sulfonamides of formula I:

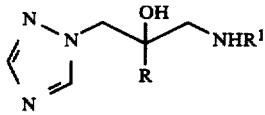

in which:

X represents N or CH;

$R^1$ represents $C_1-C_6$ alkyl, $C_1-C_4$ haloalkyl, $C_3-C_6$ cycloalkyl, 1,2,4-triazol-1-yl-$C_1-C_6$-alkyl, phenyl-$C_1-C_4$-alkyl, a phenyl-$C_1-C_4$-alkyl group where the phenyl ring carries a substituent (a)below specified, phenyl, naphtyl, a phenyl ring substituted with one or more groups (a) below specified, quinolyl, isoquinolyl, or a 5 or 6-membered heterocycle of which 1 to 3 atoms are nitrogen and/or oxygen and/or sulfur, said heterocycle being non-substituted or carrying from 1 to 3 substituents (b) below defined;

$R^2$ represents hydrogen or $C_1-C_6$ alkyl, $C_3-C_7$-cycloalkylmethyl, $C_3-C_6$ cycloalkyl, $C_1-C_4$ haloalkyl, phenyl-$C_1-C_4$-alkyl, a phenyl-$C_1-C_4$-alkyl group where the phenyl ring carries a substituent (a) below specified, pyridyl-$C_1-C_4$alkyl, furyl-$C_1-C_4$-alkyl, thienyl-$C_1-C_4$-alkyl, thiazolyl-$C_1-C_4$-alkyl, phenyl, naphtyl, a phenyl ring substituted with one or more groups (a) below specified, naphtyl, quinolyl, isoquinolyl, or a 5 or 6-membered heterocycle of which 1 to 3 atoms are nitrogen and/or oxygen and/or sulfur, said heterocycle being non-substituted or carrying from 1 to 3 substituents (b) below defined;

or $R^1$ and $R^2$ together with the nitrogen atom to which they are attached form a ring that can be fused with a benzo group;

$R^3$ is hydrogen or $R^2$ and $R^3$ together may form an oxazolidine ring as seen in formula Ia

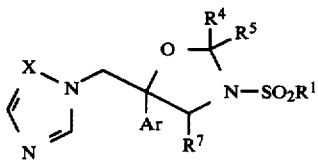

where $R^4$ is hydrogen, $C_1-C_6$ alkyl or (1H-1,2,4-triazol-1-yl)methyl, and $R^5$ is hydrogen, $C_1-C_6$ alkyl, phenyl or a phenyl group substituted with a substituent (a) below specified;

$R^7$ represents hydrogen or $C_1-C_6$ alkyl;

Ar represents phenyl or a phenyl ring substituted with one or more halogen or trifluoromethyl groups;

Substituents (a):

$C_1-C_4$ alkyl, $C_1-C_4$ haloalkyl, $C_1-C_4$ alkoxy, $C_1-C_4$ haloalkoxy, halogen, $CF_3$, $NO_2$, CN, OH, $OCH_2Ph$, $CH_2OH$, NHAc, a group of formula —$CH_2$—OCO—$R^6$, a group of formula —CO—$R^6$, a group of formula —COO—$R^6$, a group of formula—$SO_zR^6$, $NH_2$, $NHR^6$, or $NR^6_2$.

Substituents (b)

$C_1-C_4$ alkyl, $C_1-C_4$ haloalkyl, halogen, $NO_2$, CN, $NH_2$.

$R^6$ represents $C_1-C_4$ alkyl;

z is 0, 1 or 2.

and their acid addition salts.

The invention also provides the use in the treatment or prophylaxis of fungal diseases in animals and man of at least one compound of formula I or a pharmaceutically acceptable salt thereof. The invention further provides their use in the treatment or prophylaxis of fungal diseases in plants.

The invention still further provides a pharmaceutical composition comprising an effective amount of at least one compound of formula I or a pharmaceutically acceptable acid addition salt thereof in admixture with a pharmaceutically acceptable carrier or diluent.

The invention also provides a process for preparing the compounds of formula I, which in general terms comprises reacting a compound of formula IIA (obtained according to patent EP 97,469, patent EP 54,974, or patent EP 332,387) or IIB (obtained according to patent ES 334509/91 or according to patent EP 332,387)

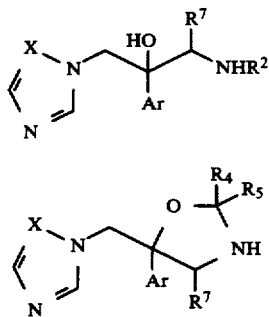

(where X, $R^2$, $R^4$, $R^5$, $R^7$ and Ar have the previously defined meaning) with a compound of formula $ClSO_2R^1$ (where $R^1$ is as defined above) to give a compound of formula I.

In the compounds of the present invention, X represents a nitrogen atom or a CH group, but preferably is a nitrogen atom.

In the compounds where $R^1$ or $R^2$ represent $C_1$-$C_6$ alkyl this can be a linear or branched alkyl chain containing from 1 to 6 carbon atoms. Examples include methyl, ethyl, propyl, i-propyl, butyl, i-butyl, sec-butyl, t-butyl, pentyl, i-pentyl, neopentyl and hexyl groups, of which methyl, ethyl and butyl are preferred, and methyl and ethyl are most preferred.

In the compounds in which $R^1$ or $R^2$ represent $C_1$-$C_4$ haloalkyl this can be a linear or branched chain and carry from 1 to 4 carbon atoms. Examples include trifluoromethyl, trichloromethyl, fluoromethyl, chloromethyl, bromomethyl, iodomethyl, difluoromethyl, dichloromethyl, 2-chloro-ethyl, 2,2-dichloroethyl, 2,2,2-trichloroethyl, pentachloroethyl, 2-fluoro-ethyl, 2,2-difluoroethyl, 2,2,2-trifluoroethyl, pentafluoroethyl, 3-chloro-propyl, 3,3-dichloropropyl, 3,3,3-trichloropropyl, 3,3,3,2,2-pentachloropropyl, 3-fluoropropyl, 3,3-difluoropropyl, 3,3,3-trifluoropropyl, pentafluoropropyl, 4-chlorobutyl, 4-fluorobutyl, 4-iodobutyl and 4-bromobutyl of which the 3-chloropropyl group is preferred.

In the compounds in which $R^1$ or $R^2$ represent a $C_3$-$C_6$ cycloalkyl group, this can be cyclopropyl, cyclobutyl, cyclopentyl or cyclohexyl, of which cyclopentyl and cyclohexyl are preferred.

In the compounds where $R^1$ or $R^2$ represent a substituted phenyl ring the substituent(s) can be any of the substituents (a) defined above, and when there are more than one, they can be the same or different. When the substituent is an halogen atom this can be fluorine, chlorine, bromine or iodine, preferably fluorine or chlorine. In the case where the substituent is a $C_1$-$C_4$ alkyl group, this can be any of the above mentioned for $R^1$ or $R^2$, but a methyl group is preferred. Thus, examples of substituted phenyl rings include 4-methylphenyl, 2,4,6-trimethylphenyl, 4-fluorophenyl, 4-chlorophenyl, 4-bromophenyl, 4-iodophenyl, 2,4-difluorophenyl, 3,4-difluorophenyl, 2,4-dichloro-5-fluorophenyl, 2,4-dichlorophenyl, 2,5-dichlorophenyl, pentafluorophenyl, 3,5-dichloro-2-hydroxyphenyl, 3-(trifluoromethyl)-phenyl, 4-(trifluoromethyl)phenyl, 4-(trichloromethyl)-phenyl, 2-fluoro-5-(trifluoromethyl)phenyl, 2-fluoro-4-(trifluoromethyl)phenyl, 3-fluoro-4-(trifluoromethyl)-phenyl, 4-(difluoromethoxy)phenyl, 4-(trifluoromethoxy)phenyl, 4-(2,2,2-trifluoroethoxy)phenyl, 4-(2,2,3,3-tetrafluoropropoxy)phenyl, 4-methoxyphenyl, 3-nitrophenyl, 2-fluoro-4-nitrophenyl, 2-nitro-4-trifluoromethylphenyl, 3-cyanophenyl, 4-cyanophenyl, 2-chloro-4-cyanophenyl, 4-(methoxycarbonyl)phenyl, 2-fluoro-4-(ethoxycarbonyl)phenyl, 4-(methylthio)phenyl, 4-(methylsulfinyl)phenyl, 4-(methylsulfonyl)phenyl, 4-acetamidophenyl, and 4-(dichloroacetamido)phenyl. The preferred substituted phenyl rings are 4-methylphenyl, 4-fluorophenyl, 4-chlorophenyl, 4-(trifluoromethyl)phenyl, 4-methoxy-phenyl, 2-nitro-4-(trifluoromethyl)phenyl, 2,5-dichlorophenyl, 4-acetamidophenyl, 3,5-dichloro-2-hydroxyphenyl, 2,4,6-trimethylphenyl and 2-fluoro-4-(trifluoromethyl)phenyl.

In the compounds where $R^1$ or $R^2$ represent a 5 or 6-membered heterocycle containing 1 to 3 nitrogen and/or oxygen and/or sulfur atoms in the cycle frame, and this heterocycle may be substituted or not by a substituent(s) (b) above defined, said $R^1$ or $R^2$ groups can be a thienyl, furanyl, piranyl, pyrrolyl, imidazolyl, pirazolyl, thiazolyl, isothiazolyl, oxazolyl, isoxazolyl, pyridyl, pyrazinyl, quinolinyl, pyrimidinyl, pyridazinyl, furazanyl, pyrrolidinyl, pyrrolinyl, imidazolidinyl, imidazolinyl, pyrazolidinyl, pyrazolinyl, piperidyl, morpholinyl, or thiomorpholinyl group, of which pyridinyl, quinolinyl, thienyl and thiazolyl are preferred.

In the compounds in which $R^2$ represents phenyl-$C_1$-$C_4$-alkyl where the phenyl ring may be substituted with a group (a) above specified, $R^2$ can be benzyl, 4-chlorobenzyl, 4-fluorobenzyl, 4-(trifluoromethyl)benzyl, 1-phenylethyl, 2-phenylethyl, 3-phenylpropyl, 2-phenylpropyl, 1-phenylpropyl, 4-phenylbutyl, 3-phenylbutyl, 2-phenylbutyl, 1-phenylbutyl, but preferably is benzyl, 4-chlorobenzyl, 4-fluorobenzyl, 4-(trifluoromethyl)benzyl or 2-phenylethyl.

In the compounds in which $R^2$ represents pyridyl-$C_1$-$C_4$-alkyl this can be 2-pyridylmethyl, 3-pyridylmethyl, 4-pyridylmethyl, 2-(2-pyridyl) ethyl, 2-(3-pyridyl)ethyl, 2-(4-pyridyl)ethyl, 3-(2-pyridyl)propyl, 3-(3-pyridyl)propyl, 3-(4-pyridyl)propyl or 4-(2-pyridyl)butyl, of which 2-pyridylmethyl, 3-pyridylmethyl and 2-(3-pyridyl)ethyl are preferred.

In the compounds in which $R^2$ represents furyl-$C_1$-$C_4$-alkyl this can be 2-furylmethyl, 2-(2-furyl)ethyl, 3-(2-furyl)propyl, 4-(2-furyl)butyl, of which 2-furylmethyl is preferred.

In the compounds where $R^1$ and $R^2$ together with the nitrogen atom to which they are attached form a ring that can be fused with a benzo group, said $R^1$-N-$R^2$ group can be a 1,1-dioxotetrahydroisothiazolidin-2-yl or a benzo-1,1,3-trioxotetrahydroisothiazolidin-2-yl group.

In those compounds where $R^2$ and $R^3$ may form an oxazolidine ring as seen in formula Ia

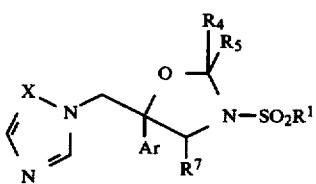

where $R^4$ is hydrogen, $C_1$-$C_6$ alkyl or (1H-1,2,4-triazol-1-ylmethyl, and $R^5$ is hydrogen, $C_1$-$C_6$ alkyl, phenyl or a phenyl group substituted with a substituent (a) above specified, those in which $R^4$ is hydrogen and $R^5$ is hydrogen, methyl, phenyl or 4-chlorophenyl are preferred.

In the compounds where $R^7$ represents hydrogen or a $C_1$-$C_6$ alkyl group, said alkyl group can be a linear or a branched alkyl chain containing 1 to 6 carbon atoms. Examples include methyl, ethyl, propyl, i-propyl, butyl, i-butyl, sec-butyl, t-butyl, pentyl, i-pentyl, neopentyl and hexyl groups, preferably methyl, ethyl and butyl, and more preferably methyl.

In the compounds of the present invention Ar represents a phenyl group or a phenyl group substituted by one or more halo or trifluoro-methyl groups. The halogen atoms can be fluor, chloro, bromo and iodo, of which fluor and chloro are preferred. The phenyl ring can carry one or more substituents of this type, and they can be the same or different. When the phenyl ring is substituted, said substituent(s) can be in any of the available positions of the ring, but positions 2 and 4 are preferred. Examples include 4-(trifluoromethyl)phenyl, 4-fluorophenyl, 4-chlorophenyl, 2-chloro-4-fluorophenyl, 4-chloro-2-fluorophenyl, 4-bromophenyl, 2-fluoro-4-iodophenyl, 2,4-dichlorophenyl, 2,4-dichloro-5-fluorophenyl, 2,4-difluorophenyl, 2-fluoro-4-(trifluoromethyl)phenyl, and 2-fluoro-3-(trifluoromethyl)phenyl, of which 4-(trifluoromethyl)phenyl, 2-fluoro-4-(trifluoromethyl)phenyl, 4-fluorophenyl, 2-chloro-4-fluorophenyl, 2,4-dichlorophenyl, 2,4-difluorophenyl, 2,4-dichloro-5-fluorophenyl and 4-chlorophenyl are preferred, and 2,4-dichlorophenyl, 2,4-difluorophenyl and 4-chlorophenyl are the most preferred.

A preferred group of compounds of the present invention comprises compounds of formula I wherein X is nitrogen, $R^3$ is hydrogen, $R^7$ is methyl, Ar is 4-(trifluoromethyl)phenyl, 4-fluorophenyl, 2-chloro-4-fluorophenyl, 2,4-dichlorophenyl, 2,4-difluorophenyl, 2-fluoro-4-(trifluoromethyl)phenyl or 4-chlorophenyl, and $R^2$ and $R^1$ are as defined above.

Another preferred group of compounds of the present invention comprises compounds of formula I wherein X is nitrogen, $R^7$ is methyl, Ar is 4-(trifluoromethyl)phenyl, 4-fluorophenyl, 2-chloro-4-fluorophenyl, 2,4-dichlorphenyl, 2,4-difluorophenyl, 2-fluoro-4-(trifluoromethyl)phenyl or 4-chlorphenyl, $R^1$ is as defined above and $R^2$ and $R^3$ form an oxazolidine ring as seen in the formula

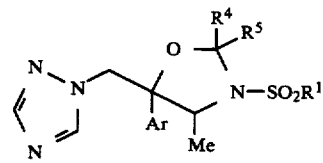

where $R^4$ and $R^5$ are as defined above, but preferably they are both a hydrogen atom.

Examples of specific compounds of the present invention are given in Tables I-II (the accompanying numbers stand for the example in which their preparation is described):

TABLE I

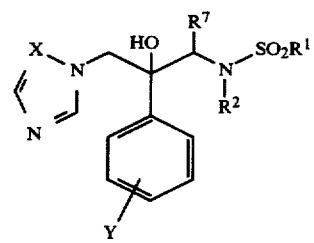

| Ex. | X | Y | $R^2$ | $R^1$ | $R^7$ | salt |
|---|---|---|---|---|---|---|
| 1 | N | 2,4-diF | H | Me | H | oxalate |
| 2 | N | 2,4-diF | H | 4-MeC$_6$H$_4$ | H | — |
| 3 | N | 2,4-diF | H | 3-Cl-propyl | H | oxalate |
| 4 | | | | | | |

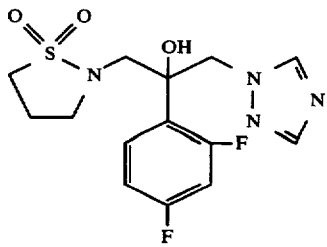

TABLE I-continued

[Structure: General formula with X-N heterocycle-CH2-C(OH)(Ph-Y)-CH(R7)-N(R2)(SO2R1)]

| Ex. | X | Y | R² | R¹ | R⁷ | salt |
|---|---|---|---|---|---|---|
| 5 | | | | [Structure: benzisothiazole-1,1-dioxide-N-CH2-C(OH)(2,4-diF-C6H3)-CH2-N(triazole)] | | (CO2H)2 |
| 6 | N | 2,4-diCl | H | 4-Me—C6H4 | H | oxalate |
| 7 | N | 2,4-diF | H | 4-F—C6H4 | H | — |
| 8 | N | 2,4-diCl | H | 4-F—C6H4 | H | oxalate |
| 9 | N | 2,4-diF | H | 4-Cl—C6H4 | H | oxalate |
| 10 | N | 2,4-diCl | H | 4-Cl—C6H4 | H | — |
| 11 | N | 2,4-diCl | H | 4-MeO—C6H4 | H | — |
| 12 | N | 2,4-diCl | H | 4-F3C-2-NO2—C6H3 | H | — |
| 13 | N | 2,4-diCl | H | 2,5-diCl—C6H3 | H | — |
| 14 | N | 2,4-diCl | H | 4-AcNH—C6H4 | H | — |
| 15 | N | 2,4-diCl | H | 3,5-diCl-2-HO—C6H2 | H | — |
| 16 | N | 2,4-diCl | H | 2,4,6-triMe—C6H2 | H | — |
| 17 | N | 2,4-diCl | H | Me | H | — |
| 18 | N | 2,4-diCl | H | Et | H | — |
| 19 | N | 2,4-diCl | H | n-Pr | H | — |
| 20 | N | 2,4-diCl | H | n-Bu | H | — |
| 21 | N | 2,4-diF | H | 2-thienyl | H | — |
| 22 | N | 2,4-diCl | H | 2-thienyl | H | — |
| 23 | N | 2,4-diCl | H | 8-quinolyl | H | — |
| 24 | N | 2,4-diCl | H | 2-AcNH-5-thiazolyl | H | — |
| 25 | N | 2,4-diCl | H | 3-Cl-propyl | H | oxalate |
| 26 | | | | [Structure: isothiazolidine-1,1-dioxide-N-CH2-C(OH)(2,4-diCl-C6H3)-CH2-N(triazole)] | | |
| 27 | N | 2,4-diCl | H | 3-(1,2,4-triazol-1-yl)propyl | H | — |
| 28 | N | 2,4-diCl | H | 2-naphtyl | H | — |
| 29 | N | 2,4-diCl | H | 4-F3C—C6H4 | H | — |
| 30 | N | 2,4-diF | H | 4-F3C—C6H4 | H | — |
| 31 | N | 2,4-diCl | Me | Me | H | — |
| 32 | N | 2,4-diCl | i-Pr | Me | H | — |
| 33 | N | 2,4-diCl | i-Bu | Me | H | — |
| 34 | N | 2,4-diCl | i-Bu | 4-F3C—C6H4 | H | — |
| 35 | N | 2,4-diCl | Bn | Me | H | — |
| 36 | N | 2,4-diCl | 4-Cl—Bn | Me | H | — |
| 37 | N | 2,4-diCl | 4-F3C—Bn | Me | H | — |
| 38 | N | 2,4-diCl | 4-F—Bn | Me | H | — |
| 39 | N | 2,4-diCl | PhCH2CH2 | Me | H | — |
| 40 | N | 2,4-diCl | 2-pyr-CH2 | Me | H | — |
| 41 | N | 2,4-diCl | 2-pyr-CH2CH2 | Me | H | — |
| 42 | N | 2,4-diCl | 2-furyl-CH2 | Me | H | — |
| 43 | N | 2,4-diCl | c-C6H11—CH2 | Me | H | — |
| 44 | N | 2,4-diCl | H | Me | Me | — |
| 45 | N | 2,4-diCl | H | 4-Cl—C6H4 | Me | — |

TABLE II

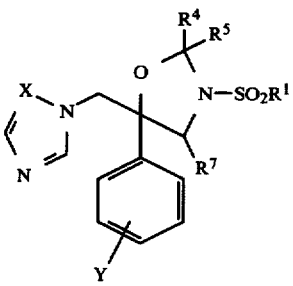

| Ex. | X | Y | R⁴ | R⁵ | R¹ | R⁷ | salt |
|---|---|---|---|---|---|---|---|
| 46 | N | 2,4-diCl | H | H | Me | H | — |
| 47 | N | 2,4-diCl | H | H | 4-F₃CC₆H₄ | H | — |
| 48 | N | 2,4-diCl | H | Me | Me | H | oxalate |
| 49 | N | 2,4-diCl | H | Me | 4-F₃CC₆H₄ | H | — |
| 50 | N | 2,4-diCl | H | 4-Cl—C₆H₄ | Me | H | — |
| 51 | N | 2,4-diCl | H | H | Me | Me | — |
| 52 | N | 2,4-diCl | H | Me | Me | Me | — |
| 55 | N | 2,4-diF | H | H | Me | Me | — |

Of the compounds listed above, the following are preferred, that is to say Compounds No. 1, 17, 18, 19, 20, 31, 32, 33, 35, 36, 37, 38, 39, 40, 41, 44, 45, 46, 47 and 51 and 55.

The most preferred compounds are:

No. 17: 2-(2,4-Dichlorphenyl)-3-(methanesulfonamido-1-(1H-1,2,3-triazol-1-yl)propan-2-ol;

No. 32: 2-(2,4-Dichlorophenyl)-3-(N-iso-propylmethanesulfonamido)-1-(1H-1,2,4-triazol-1-yl)propan-2-ol No. 44: (2R*,3R*)2-(2,4-Dichloropheny)-3-methanesulfonamido-1-(1H-1,2,4-triazol-1-yl)butan-2-ol;

No. 45: (2R*,3R*)-3-(4-Chlorobenzenesulfonamido)-2-(2,4-dichlorophenyl)-1-(1H-1,2,4-triazol-1-yl)butan-2-ol;

No. 46: 5-(2,4-Dichlorphenyl)-3-methanesulfonyl-5-[(1H-1,2,4-triazol-1-yl]methyl)oxazolidine;

No. 51: (4R*,5R*)-5-(2,4-Dichlorophenyl)-3-methanesulfonyl-4-methyl-5-[(1H-1,2,4-triazol-1-yl]methyl) oxazolidine.

No. 55: (4R*,5R*)-5-(2,4-Difluorophenyl)-3-methanesulfonyl-4-methyl-5-(LIH-1,2,3-triazol-1-yl]methyl) oxazolidine.

The compounds of the present invention contain one or more basic nitrogen atoms than can form pharmaceutically acceptable addition salts with a variety of acids, all of which salts are included in the present invention. Examples of preferred salts include the hydrochloride, sulfate, nitrate, oxalate, maleate, fumarate, p-toluenesulfonate, methylsulfonate and perchlorate salts.

The presence of one or more asymmetric centers in the compounds of the present invention implies the existence of stereisomers. The present invention covers both the individual stereoisomers and mixtures thereof (e.g. racemic mixtures), being irrelevant if they have been obtained by synthesis or prepared physically mixing them up.

The compounds of the present invention can be obtained according to several conventional methods. Appropriate reagents and reaction conditions for their performance and procedures for isolating the desired products will be well known to those skilled in the art, in accordance with the literature precedents. Usually, the precise method used for the preparation of a given compound will depend upon its chemical structure, but in general they can be obtained as follows:

The compounds of the present invention can be prepared from amine IIA or IIB by treatment with a sulfonyl chloride of formula $ClSO_2R^1$ (where $R^1$ is as above defined). The starting amines can be prepared according to the procedures described in patents EP 97,469 (IIA, X=N, $R^2$=H), EP 54,974 (IIA, X=CH, $R^2 \neq H$, EP 332,387 (IIB, $R^4 = R^5 = H$, or ES 334509/91 (IIB, $R^4$ and/or $R^5 \neq H$). The chemical reaction between amine II and the corresponding sulfonyl chloride is performed under standard reaction conditions for the formation of the sulfonamide bond. Thus, the amine is dissolved in an inert solvent containing a proton scavanger base. The solvent can be any of the commonly used solvents for this type of reactions, provided that it is compatible with the reactants. Halogenated hydrocarbons, such as dichloromethane or chloroform, are preferred. As far as the base is concerned, the use of triethylamine is preferred. The reaction can take place within a wide range of temperatures and reaction times. We have found that a temperature comprised between −10° C. and room temperature during a period of time from 5 rain to 18 h is usually enough to obtain a good to excellent yield of the final product.

The pharmaceutically acceptable salts of the compounds of formula I are obtained by addition of the corresponding acid into a solution of the amine in a solvent in which the salt precipitates.

According to the antifungal activity of the compounds of formula I, the present invention further provides compositions that contain one or more of the compounds of the present invention, together with a carrier and optionally other auxilliary agents, if necessary. The compounds of the present invention can be administered in different formulations, the precise nature of which will depend upon the chosen route of administration. Thus, solid compositions according to the present invention for oral administration include compressed tablets, dispersible powders, granules and capsules. In tablets, one or more of the active component(s) is admixed with at least one inert diluent such as lactose, starch, mannitol, microcrystalline cellulose or calcium phosphate; granulating and desintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides. Soft gelatin capsules are possible wherein the active ingredient is mixed with water or an oil medium, for example peanut oil, liquid paraffin or olive oil.

Dispersible powders and granules suitable for preparation of a suspension by the addition of water provide the active ingredient in admixture with a dispersing or wetting agent, a suspending agent, such as sodium carboxymethylcellulose, sodium alginate, polyvinylpirrolidone, gum tragacanth, xantham gum, gum acacia, and one or more preservatives, such as methyl or n-propyl-p-hydroxybenzoate. Additional excipients, for example sweetening, flavoring and coloring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise adjuvants such as wetting agents, suspending agents, sweetening, flavoring, perfuming, preserving agents and buffers.

Other compositions for oral administration include spray compositions, which may be prepared by known methods and which comprise one or more active compound(s). The spray compositions will contain a suitable propellent.

Preparations for injection according to the present invention for parenteral administration include sterile aqueous or non-aqueous solutions, suspensions or emulsions, in a non-toxic parentally-acceptable diluent or solvent. Examples of aqueous solvents or suspending media are distilled water for injection, the Ringer's solution, and an isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by one of the known methods or manufactured in the form of sterile solid compositions which can be dissolved in sterile water or some other sterile injectable medium immediately before use. When all of the components are sterile, the injectables will maintain the sterility if they are manufactured in sterile environment.

A compound of the invention may also be administered in the form of suppositories for rectal administration of the drug, or as creams, ointments jellies, sprays, solutions or suspensions for topical use and pessaries for vaginal administration.

The dosage and frequency of dose may vary depending upon the nature of the fungal disease, the precise activity of the compound of formula I, symptoms, age and body weight of the patient, as well as upon the route of administration. Thus, for oral and parenteral administration to human patients the daily dose will be from 1 mg to 1 g for an adult, preferably a dosage of from 5 to 500 mg, which may be administered either as a single dose or as divided doses. A preferred dosage for human patients is from 0.010 to 20 mg/kg of body weight. For topical administration, a cream or ointment containing 1-10% of a compound of formula I will be applied to the skin from one to three times daily.

Preferred pharmaceutical or veterinary compositions of the invention are compositions suitable for oral administration, and particularly tablets and capsules containing from 1 to 1000 mg of a compound of the present invention.

The compounds of the present invention and their salts are antifungal agents, useful in the curative or prophylactic treatment of fungal infections in animals, including man, and plants. For example, they are useful in treating topical fungal infections in man caused by, among other organisms, species of *Candida, Rhodotorula, Torulopsis, Trychophyton, Microsporum* or *Epidermophyton,* or in mucosal infections caused by *Candida albicans* (e.g. oral thrush and vaginal candidiasis). They can be used in the treatment of sistemic fungal infections caused by, for example, *Candida albicans, Cryptococcus neoformans, Aspergillus flayus, Aspergillus furnigatus, Coccidioides, Paracoccidioides, Histoplasrna* or *Blastornyces.*

The in vitro activity of the compounds of the present invention can be determined by calculating their minimum inhibitory concentration (MIC), that is, the minimun concentration of compound needed to completely inhibit the growth of the fungus in a suitable medium. The in vivo activity evaluation can be carried out by determining the protection from death after the oral administration of a compound of formula I to mice that have been previously inoculated with a lethal dose containing a strain of *Candida albicans.*

The compounds of the present invention also possess antifungal properties which are useful in combatting a wide variety of plant fungal diseases. The invention thus provides the use of a compound of formula I for the treatment or prophylaxis of fungal infections in plants. The invention still further provides a plant fungicidal composition comprising a non-pharmaceutical carrier or diluent in admixture with at least one compound of formula I.

The invention also provides a method of combatting fungal diseases in a plant, which comprises applying to the plant, to seed of the plant or to the locus of the plant or seed at least one compound of general formula I. The term "plant" as used herein includes seedlings, bushes and trees. Furthermore, the fungicidal method of the invention includes preventative, protectant, prophylactic and eradicant treatment.

The invention is further illustrated by the following examples, which describe the preparation of various of the compounds of the invention, as well as the preparations of some of the starting materials. Two biological examples further illustrate the activity of the compounds of the present invention.

EXAMPLE 1

2-(2,4-Difluorophenyl)-3-(methanesulfonamicio)-1-(1H-1,2,4-triazol-1-yl)propan-2-ol, oxalate To a cooled solution (0° C.) containing 2-(2,4-difluorophenyl)-3-amino-1-(1H-1,2,4-triazol-1-yl)propan-2-ol (0.5 g, 1.96 mmol) in dry dichloromethane (7 mL) it was added triethylamine (0.55 mL, 3.93 mmol) and methanesulfonyl chloride (0.17 mL, 2.16 mmol) and the mixture was stirred at 0° C. for 1 h and then at room temperature for 10 h. Next, a solution of aqueous saturated ammonium chloride was added and the organic phase was separated. This was dried over anhydrous sodium sulfate, the drying agent was filtered, and the filtrate was concentrated to a paste that was purified by flash chromatography. The resulting oil (570 mg, 87%) was treated with a solution of oxalic acid and let it precipitate overnight at $-20°$ C. The white precipitate was filtered and dried to afford 507 mg of the title product. mp 56°-64° C.; $^1$H NMR (80 MHz, CD$_3$OD)$\delta$(TMS) 8.42 (s, 1H, N=CH), 7.83 (s, 1H, N=CH), 7.7-7.3 (m, 1H, arom.), 7.2-6.7 (m, 2H, atom.), 4.73 (s, 2H, CH$_2$-Tr), 3.60 (s, 2H, CH$_2$NH), 2.89 (s, 3H, MeSO$_2$). Anal calcd. for C$_{12}$H$_{14}$F$_2$N$_4$O$_3$S.(COOH)$_2$.-H$_2$O: C 38.18%; H 4.12%; N 12.72%. Found: C 38.21%; H 4.26%; N 12.39%.

EXAMPLE 2

2-(2,4-Difluorophenyl)-3-(4-methylbenzenesulfonamido)-1-(1H-1,2,4-triazol-1-yl)propan-2-ol Following the procedure described in example 1 but using p-toluenesulfonychloride instead of methanesulfonylchloride, the title compound was obtained in a similar yield: mp 130°–136° C.; $^1$H NMR (80 MHz, CDCl$_3$)δ(TMS) 8.17 (s, 1H, N=CH), 7.66 (d, J=9.2 Hz, 3H, N=CH, arom), 7.5–7.3 (m, 3H, arom.), 6.9–6.5 (m, 2H, atom.), 4.68 (s, 2H, CH$_2$-Tr), 3.36 (s, 2H, CH$_2$NH), 2.42 (s, 3H, MePh). Anal calcd. for C$_{18}$H$_{18}$F$_2$N$_4$O$_3$S: C 52.94%; H 4.44%; N 13.72%. Found: C 52.92%; H 4.48%; N 13.37%.

EXAMPLE 3

3-(3-Chloropropanesulfonamido)-2-(2,4-difluorophenyl)-1-(1H-1,2,4-triazol-1-yl)propan-2-ol, oxalate Following the procedure described in example 1 but using 3-chloropropylsulfonylchloride instead of methanesulfonylchloride, the title compound was obtained in a similar yield: mp 138°–139° C.; $^1$H NMR (80 MHz, CD$_3$OD)δ(TMS) 8.34 (s, 1H, N=CH), 7.79 (s, 1H, N=CH), 7.6–7.3 (m, 1H, arom.), 7.1–6.7 (m, 2H, arom.), 4.71 (s, 2H, CH$_2$-Tr), 3.64 (t, J=6.5, Hz, 2H, CH$_2$SO$_2$), 3.61 (s, 2H, CH$_2$NH), 3.4–3.0 (m, 2H, ClCH$_2$), 2.11 (quint. J=6.5 Hz, 2H, ClCH$_2$CH$_2$). Anal. calcd. for C$_{14}$H$_{17}$ClF$_2$N$_4$O$_3$S.(CO$_2$H)$_2$: C 39.64%; H 3.95%; N 11.56%. Found: C 39.72%; H 3.88%; N 11.44%.

EXAMPLE 4

2-(2,4-Difluorophenyl)-3-(1,1-dioxotetrahydroisothiazolidin-2-yl)-1-(1H-1,2,4-triazol-1-yl)propan-2-ol A solution containing the free base of the compound of the previous example (507 mg, 1.28 mmol) in ethanol (20 mL) was treated at 70° C. with sodium ethoxide (632 mg, 1.6 mmol) for 2 h. The solvent was removed and the residue was partitioned between water and dichloromethane. The organic phase was separated, it was dried over anhydrous sodium sulfate, the drying agent was filtered, and the flitrate was concentrated to a white solid that was purified by flash chromatography. mp 134°–136 ° C.; $^1$H NMR (80 MHz, CDCl$_3$)δ(TMS) 8.01 (s, 1H, N=CH), 7.80 (s, 1H, N=CH), 7.6–7.3 (m, 1H, arom.), 7.0–6.6 (m, 2H, atom.), 4.75 (AB system, Δv=0.18, J=14.4 Hz, 2H, CH$_2$-Tr), 3.8–3.0 (m, 6H, NCH$_2$CH$_2$CH$_2$S, NCH$_2$C(OH)), 2.30 (quint. J=7.2 Hz, 2H, SCH$_2$CH$_2$). MS (CI, NH$_3$): M$^+$+1=359 Anal. calcd. for C$_{14}$H$_{16}$F$_2$N$_4$O$_3$S: C 46.92%; H 4.50%; N 15.63%. Found: C 46.72%; H 4.48%; N 15.58%.

EXAMPLE 5

3-(Benzo-1,1,3-trioxotetrahydroisotiazolydin-2-yl)-2-(2,4-difluorophenyl)-1-(1H-1,2,4-triazol-1-yl)propan-2-ol, oxalate Following the procedure described in example 1 but using 2-sulfobenzoic add mixed anhydride instead of methanesulfonylchloride, the title compound was obtained in a similar yield: mp 172°–181° C.; $^1$H NMR (80 MHz, CDCl$_3$)δ(TMS) 9.1–8.2 (m, 1H, arom.), 8.1–7.9 (m, 2H, arom.) 8.02 (s, 1H, N=CH), 7.7–7.4 (m, 3H, N=CH, arom.), 7.1–6.7 (m, 2H, arom.), 5.06 (AB system, Δv=0.32, J=14 Hz, 2H, CH$_2$-Tr), 3.95 (AB system, Δv=0.68, J=14 Hz, 2H, CH$_2$N). Anal. calcd. for C$_{18}$H$_{14}$F$_2$N$_4$O$_4$S (CO$_2$H)$_2$: C 47.25%; H 2.78%; N 11.02%. Found: C 47.12%; H 2.83%; N 11.05%.

EXAMPLE 6

2-(2,4-Dichlorophenyl)-3-(4-methylbenzenesulfonamido)-1-(1H-1,2,4-triazol-1-yl)propan-2-ol, oxalate Following the procedure described in example 3 but using 2-(2,4-dichlorophenyl)-3-amino-1-(1H-1,2,4-triazol-1-yl)propan-2-ol instead of 2-( 2,4-difluorophenyl)-3-amino-1-(1H-1,2,4-triazol-1-yl)propan-2-ol, and precipitating the resulting oil with oxalic acid, the title compound was obtained: mp 91°–102° C.; $^1$H NMR (80 MHz, CDCl$_3$)δ(TMS) 8.31 (s, 1H, N=CH), 7.7–7.0 (m, 8H, N=CH, atom.), 4.77 (s, 2H, CH$_2$-Tr), 3.61 (s, 2H, CH$_2$NH), 2.42 (s, 3H, MePh). Anal calcd. for C$_{18}$H$_{18}$Cl$_2$N$_4$O$_3$S.(CO$_2$H)$_2$.1/4Et$_2$O: C 45.85%; H 4.10%; 10.19N %. Found: C 45.88%; H 4.40%; N 10.01%.

EXAMPLE 7

2-(2,4-Difluorophenyl)-3-(4-fluorobenzenesulfonamido)-1-(1H-1,2,4-triazol-1-yl)propan-2-ol Following the procedure described in example 1 but using p-fluorobenzenesulfonylchloride instead of methanesulfonylchloride, the title compound was obtained in a similar yield: mp 140°–146° C.; $^1$H NMR (80 MHz, MeOH-d$_4$)δ(TMS) 8.11 (s, 1H, N=CH), 7.9–7.0 (m, 8H, N=CH, arom.), 4.68 (s, 2H, TrCH$_2$), 3.58 (s, 2H, CH$_2$NH) Anal calcd. for C$_{17}$H$_{15}$F$_3$N$_4$O$_3$S: C 49.51%; H 3.67%; 13.59N %. Found: C 49.88%; H 3.93%; N 13.40%.

EXAMPLE 8

2-(2,4-Dichlorophenyl)-3-(4-fluorobenzenesulfonamido)-1-(1H-1,2,4-triazol-1-yl)propan-2-ol, oxalate Following the procedure described in example 7 but using 2-(2,4-dichlorophenyl)-3-amino-1-(1H-1,2,4-triazol-1-yl)propan-2-ol instead of 2-(2,4-difluorophenyl)-3-amino-1-(1H-1,2,4-triazol-1-yl)propan-2-ol, and precipitating the resulting oil with oxalic acid, the title compound was obtained in a similar yield: mp 62°–74° C.; $^1$H NMR (80 MHz, MeOH-d$_4$)δ(TMS) 8.20 (s, 1H, N=CH), 7.9–7.1 (m, 8H, N=CH, arom.), 5.00 (AB system, Δv=0.24, J=14.4 Hz, 2H, CH$_2$-Tr), 3.51 (AB system, 2H, CH$_2$NH). Anal calcd. for C$_{17}$H$_{15}$Cl$_2$FN$_4$O$_3$S.(CO$_2$H$_2$)$_2$: C 42.63%; H 3.20%; N 10.47%. Found: C 43.01%; H 3.58%; N 12.20%.

EXAMPLE 9

3-(4-Chlorobenzenesulfonarnido)-2-(2,4-difluorophenYl)-1-(1H-1,2,4-triazol-1-yl)propan-2-ol, oxalate Following the procedure described in example 1 but using p-chlorobenzenesulfonylchloride instead of methanesulfonylchloride, the title compound was obtained in a similar yield: mp 156°–159° C.; $^1$NMR (80 MHz, MeOH-d$_4$)δ(TMS) 8.27 (s, 1H, N=CH), 7.74 (s, 1H, N=CH) 7.7–6.6 (m, 7H, arom.), 4.72 (AB system, Δv=0.22, J=15 Hz, 2H, CH$_2$-Tr), 3.41 (s, 2H, CH$_2$NH). Anal calcd. for C$_{17}$H$_{15}$ClF$_2$N$_4$O$_3$S: C 47.61%; H 3.53%; 13.06N %. Found: C 47.27%; H 3.57%; N 12.69%.

EXAMPLE 10

3-(4-Chlorobenzenesulfonamido)-2-(2,4-dichlorophenyl)-1-(1H-1,2,4-triazol-1-yl)propan-2-ol Following the procedure described in example 9 but using 2-(2,4-dichlorophenyl)-3-amino-1-(1H-1,2,4-triazol-1-yl)propan-2-ol instead of 2-(2,4-difluorophenyl)-3-amino-1-(1H-1,2,4-triazol-1-yl)propan-2-ol, the title compound was obtained in a similar yield: mp 182°–183° C.; $^1$H NMR (80 MHz, MeOH-d$_4$)δ(TMS) 8.25 (s, 1H, N=CH), 7.7–7.0 (m, 8H, N=CH, arom.), 4.89 (AB system, Δv=0.39, J=14.5 Hz, 2H, CH$_2$-Tr), 3.61 (AB system, Δv=0.18, J=14 Hz, 2H, CH$_2$NH). Anal calcd. for C$_{17}$H$_{15}$Cl$_3$N$_4$O$_3$S: C 44.22%; H 3.27%; 11.96N %. Found: C 44.76%; H 3.39%; N 12.05%.

EXAMPLE 11

2-(2,4-Dichlorophenyl)-3-(4-methoxybenzenesulfonamido)-1-(1H-1,2,4-triazol-1-yl)propan-2-ol Following the procedure described in the preceeding examples but using 2-(2,4-dichlorophenyl)-3-amino-1-(1H-1,2,4-triazol-1-yl)propan-2-ol and p-methoxybenzenesulfonylchloride, the title compound was obtained in a similar yield: mp 56°–66° C.; $^1$H NMR (80 MHz, CDCl$_3$)δ(TMS) 8.0–7.5 (m, 4H, arom), 7.3–6.9 (m, 3H, arom.), 5.24 (br s, 1H, NH), 4.96 (AB system, Δv=0.52, J=14.5 Hz, 2H, CH$_2$-Tr), 3.85 (s, 3H, OMe), 3.55 (dq, J$_d$=5.2 Hz, J$_q$=J=14 Hz, 2H, CH$_2$NH), 2.16 (s, 1H, N=CH), 2.03 (s, 1H, N=CH). Anal calcd. for C$_{18}$H$_{18}$Cl$_2$N$_4$O$_4$S: C 47.27%; H 3.97%; N 12.25 %. Found: C 47.56%; H 4.08%; N 12.09%.

EXAMPLE 12

2-(2,4-Dichlorophenyl)-3-(4-trifluromethyl-2-nitrobenzenesulfonamido)-1-(1H-1,2,4-triazol-1-yl)propan-2-ol Following the procedure described in the preceeding examples but using 2-(2,4-dichlorophenyl)-3-amino-1-(1H-1,2,4-triazol-1-yl)propan-2-ol and 2-nitro-4-trifluromethylbenzenesulfonylchloride, the title compound was obtained in a similar yield: mp 97°–105° C.; $^1$H NMR (80 MHz, CDCl$_3$)δ(TMS) 8.4–7.7 (m, 4H, arom), 7.6–6.9 (m, 3H, arom.), 6.03 (br, t, J=5 Hz, 1H, NH), 4.98 (AB system, Δv=0.66, J=14.5 Hz, 2H, CH$_2$-Tr), 3.87 (d, J=6Hz, 2H, CH$_2$NH). Anal calcd. for C$_{18}$H$_{14}$Cl$_2$F$_3$N$_5$O$_5$S; C 40.01%; H 2.61%; N 12.96%. Found: C 40.34%; H 2.84%; N 12.57%.

EXAMPLE 13

3-(2,5-Dichlorobenzenesulfonamido)-2-(2,4-dichlorophenyl)-1-(1H-1,2,4-triazol-1-yl)propan-2-ol Following the procedure described in the preceeding examples but using 2-(2,4-dichlorophenyl)-3-amino-1-(1H-1,2,4-triazol-1-yl)propan-2-ol and 2,5-dichlorobenzenesulfonylchloride, the title compound was obtained in a similar yield: mp 173°–174° C.; $^1$H NMR (80 MHz, CDCl$_3$)δ(TMS) 8.05 (s, 1H, CH=N), 7.78 (s, 1H, CH=N), 8.0–7.0 (m, 6H, arom), 4.89 (AB system, Δv=0.42, J=14.5 Hz, 2H, CH$_2$-Tr), 3.87 (AB system, Δv=0.30, J=14 Hz, 2H, CH$_2$NH). Anal calcd. for C$_{17}$H$_{14}$C$_{14}$N$_4$O$_3$S: C 41.15%; H 2.84%; N 11.29%. Found: C 40.86%; H 3.06%; N 11.28%.

EXAMPLE 14

3-(4-Acetamidobenzenesulfonamido)-2-(2,4-dichlorophenyl)-1-(1H, 1,2,4-triazol-1-yl) propan-2-ol Following the procedure described in the preceeding examples but using 3-arnino-2-(2,4-dichlorophenyl)-1-(1H-1,2,4-triazol-1-yl)propan-2-ol and 4-acetamidobenzenesulfonylchloride, the title compound was obtained in a similar yield: mp 232°–233° C.; $^1$H NMR (80 MHz, MeOH-d$_4$)δ(TMS) 8.12 (s, 1H, CH=N), 7.75 (s, 1H, CH=N), 7.68 (s, 4H, arom), 7.7–7.1 (m, 3H, arom), 4.93 (AB system, Δv=0.41, J=14.5 Hz, 2H, CH$_2$-Tr), 3.56 (d, J=2 Hz, 2H, CH$_2$NH). Anal calcd. for C$_{19}$H$_{19}$Cl$_2$N$_5$O$_4$S: C 45.97%; H 3.64%; N 14.89%. Found: C 46.30%; H 4.17%; N 14.90%.

EXAMPLE 15

3-(3,5-Dichloro-2-hydroxybenzenesulfonamido)-2-(2,4-dichlorophenyl)-1-(1H-1,2,4-triazol-1-yl)propan-2-ol Following the procedure described in the preceeding examples but using 2-(2,4-dichlorophenyl)-3-amino-1-(1H-1,2,4-triazol-1-yl)propan-2-ol and 3,5-dichloro-2-hydroxybenzenesulfonylchloride, the title compound was obtained in a similar yield: mp dec; $^1$H NMR (80 MHz, MeOH-d$_4$)δ(TMS) 8.4–8.1 (m, arom), 7.7–7.4 (m, CH=N, arom), 7.3–7.0 (m, arom), 4.76 (AB system, Δv=0.35, J=14.5 Hz, 2H, CH$_2$-Tr), 3.81 (AB system, Δv=0.72, J=14 Hz, 2H, CH$_2$NH). Anal calcd. for C$_{17}$H$_{14}$Cl$_4$N$_4$O$_4$S: C 39.87%; H 2.76%; N 10.94%. Found: C 39.75%; H 2.96%; N 10.90%.

EXAMPLE 16

2-(2,4-Dichlorophenyl)-3-(2,4,6-trimethylbenzenesulfonamido)-1-(1H-1,2,4-triazol-1-yl)propan-2-ol Following the procedure described in the preceeding examples but using 3-amino-2-(2,4-dichlorophenyl)-1-(1H-1,2,4-triazol-1-yl)propan-2-ol and 2,4,6-trimethylbenzenesulfonylchloride, the title compound was obtained in a similar yield: mp 171°–172° C.; $^1$H NMR (80 MHz, CDCl$_3$)δ(TMS) 7.94 (s, 1H, CH=N), 7.80 (s, 1H, CH=N), 7.68 (s, 4H, arom), 7.7–7.0 (m, 3H, arom), 6.88 (s, 2H, arom), 4.93 (AB system, Δv=0.32, J=14.5 Hz, 2H, CH$_2$-Tr), 3.7–3.3 (m, 2H, CH$_2$NH), 2.54 (s, 6H, 2Me), 2.29 (s, 3H, Me). Anal calcd. for C$_{20}$H$_{22}$Cl$_2$N$_4$O$_3$S: C 51.18%; H 4.72%; N 11.94%. Found: C 51.26%; H 4.98%; N 11.92%.

EXAMPLE 17

2-(2,4-Dichlorophenyl)-3-(methanesulfonamido)-1-(1H-1,2,4-triazol-1-yl)propan-2-ol Following the procedure described in example 1 but using 3-amino-2-(2,4-dichlorophenyl)-1-(1H-1,2,4-triazol-1-yl)propan-2-ol, the title compound was obtained in a similar yield: mp 185°–186° C.; $^1$H NMR (80 MHz, CDCl$_3$)δ(TMS) 8.18 (s, 1H, CH=N), 7.74 (s, 1H, CH=N), 7.7–7.0 (m, 3H, arom), 6.73 (t, J=6.4 Hz, 1H, NH), 4.90 (AB system, ΔAv=0.31, J=14.5 Hz, 2H, CH$_2$-Tr), 4.0–3.5 (m, 2H, CH$_2$NH), 2.84 (s, 3H, MeSO$_2$). Anal calcd. for C$_{12}$H$_{14}$Cl$_2$N$_4$O$_3$S: C 39.46%; H 3.86%; N 15.34%. Found: C 39.44%; H 3.99%; N 15.53%.

EXAMPLE 18

2-(2,4-Dichlorophenyl)-3-(ethanesulfonamido)-1-(1H-1,2,4-triazol-1-yl)propan-2ol Following the procedure described in example 1 but using 3-amino-2-(2,4-dichlorophenyl)-1-(1H-1,2,4-triazol-1-yl)propan-2-ol and ethanesulfonylchloride, the title compound was obtained in a similar yield: mp 144°–145° C.; $^1$H NMR (80 MHz, CDCl$_3$)δ(TMS) 7.96 (s, 1H, CH=N), 7.83 (s, 1H, CH=N), 7.62 (d, J=8.5 Hz, 1H, arom), 7.4–7.1 (m, 2H, atom), 5.00 (AB system, Δv=0.56, J=14.5 Hz, 2H, CH$_2$-Tr), 4.79 (t, J=6.4 Hz, 1H, NH), 4.1–3.5 (m, 2H, CH$_2$NH 3.00 (q, J=7.5 Hz, 2H, Et), 1.29 (t, J=7.5 Hz, 3H, Et). Anal calcd. for $C_{13}H_{16}Cl_2N_4O_3S$: C 41.17%; H 4.25%; N 14.77%. Found: C 41.24%; H 4.27%; N 14.48%.

EXAMPLE 19

2-(2,4-Dichlorophenyl)-3-(propanesulfonamido)-1-(1H-1,2,4-triazol-1-yl)propan-2-ol Following the procedure described in example 1 but using 3-amino-2-(2,4-dichlorophenyl)-1-(1H-1,2,4-triazol-1-yl)propan-2-ol and propanesulfonylchloride, the title compound was obtained in a similar yield: mp 128°–129° C.; $^1$H NMR (80 MHz, CDCl$_3$)δ(TMS) 7.99 (s, 1H, CH=N), 7.83 (s, 1H, CH=N), 7.62 (d, J=8.5 Hz, 1H, arom), 7.4–7.1 (m, 2H, arom), 5.00 (AB system, Δv=0.56, J=14.5 Hz, 2H, CH$_2$-Tr), 4.91 (m, 1H, NH, 4.1–3.5 (m, 2H, CH$_2$NH), 3.1–2.8 (m, 2H, CH$_2$S), 2.1–1.5 (m, 2H, CH$_2$CH$_2$S), 1.00 (t, J=7.5 Hz, 3H, Me). Anal calcd. for $C_{14}H_{18}Cl_2N_4O_3S$: C 42.76%; H 4.61%; N 14.25%. Found: C 42.61%; H 4.77%; N 14.08%.

EXAMPLE 20

3-Butanesulfonamido-2-(2,4-dichlorophenyl)-1-(1H-1,2,4-triazol-1-yl)propan-2-ol

Following the procedure described in example 1 but using 3-amino-2-(2,4-dichlorophenyl)-1-(1H-1,2,4-triazol-1-yl)propan-2-ol and butanesulfonylchloride, the title compound was obtained in a similar yield as a solid foam: $^1$H NMR (80 MHz, CDCl$_3$)δ(TMS) 8.00 (s, 1H, CH=N), 7.83 (s, 1H, CH=N), 7.62 (d, J=8.5 Hz, 1H, arom), 7.4–7.1 (m, 2H, arom), 5.00 (AB system, Δv=0.56, J=14.5 Hz, 2H, CH$_2$-Tr), 4.88 (t, J=6.4 Hz, 1H, NH), 4.1–3.5 (m, 2H, CH$_2$NH), 3.1–2.8 (m, 2H, NCH$_2$CH$_2$), 1.8–1.1 (m, 4H, NCH$_2$CH$_2$CH$_2$), 1.1–0.7 (m, 3H, CH$_3$). Anal calcd. for $C_{15}H_{20}Cl_2N_4O_3S$: C 44.23%; H 4.95%; N 13.76%. Found: C 44.80%; H 5.37%; N 13.16%.

EXAMPLE 21

2-(2,4-Difluorophenyl)-3-(2-thiophenesulfonamido)-1(1H-1,2,4-triazol-1-yl)propan-2-ol Following the procedure described in example 1 but using 2-thienylsulfonylchloride, the title compound was obtained as a solid foam in a similar yield: $^1$NMR (80 MHz, CDCl$_3$)δ(TMS) 8.01 (s, 1H, CH=N), 7.84 (s, 1H CH=N), 7.7–6.6 (m, 6H, arom), 5.37 (br t, 1H, NH), 4.75 (s, 2H, CH$_2$-Tr), 3.7–3.1 (m, 2H, CH$_2$NH). Anal calcd. for $C_{15}H_{14}F_2N_4O_3S_2$: C 44.99%; H 3.52%; N 13.99%. Found: C 44.51%; H 3.65%; N 14.08%.

EXAMPLE 22

2-(2,4-Dichlorophenyl)-3-(2-thiophenesulfonamido)-1-(1H-1,2,4-triazol-1-yl)propan-2-ol Following the procedure described in the preceeding example but using 3-amino-2-(2,4-dichlorophenyl)-1-(1H-1,2,4-triazol-1-yl)propan-2-ol and 2-thienylsulfonylchloride, the title compound was obtained in a similar yield: mp 169°–180° C.; $^1$H NMR (80 MHz, MeOH-d$_4$)δ(TMS) 8.19 (s, 1H, CH=N), 7.74 (s, 1H, CH=N), 7.7–7.0 (m, 6H, arom), 4–95 (AB system, Δv=0.60, J=14.5 Hz, 2H, CH$_2$-Tr), 3.68 (AB system, Δv=0.13, J=14 Hz, 2H, CH$_2$NH). Anal calcd. for $C_{15}H_{14}Cl_2N_4O_3S_2$: C 41.58%; H 3.26%; N 12.93%. Found: C 42.39%; H 3.27%; N 13.06%.

EXAMPLE 23

2-(2,4-Dichlorophenyl)-3-(8-quinolinelsulfonamido)-1-(1H-1,2,4-triazol-1-yl)propan-2-ol Following the procedure described in the preceeding examples but using 3-amino-2-(2,4-dichlorophenyl)-1-(1H-1,2,4-triazol-1-yl)propan-2-ol and 8-quinolinesulfonylchloride, the title compound was obtained in a similar yield: mp 186°–187° C.; $^1$H NMR (80 MHz, MeOH-d$_4$)δ(TMS) 8.9–8.8 (m, 1H, arom), 8.4–8.0 (m, 4H, arom, CH=N), 7.8–7.5 (m, 3H, CH=N), 7.26 (d, J=8.5 Hz, 1H, arom), 7.4–7.1 (m, 2H, arom), 4.81 (AB system, Δv=0.32, J=14.5 Hz, 2H, CH$_2$-Tr), 3.78 (AB system, Δv=0.36, J=14 Hz, 2H, CH$_2$NH). Anal calcd. for $C_{20}H_{17}Cl_2N_5O_3S$: C 50.22%; H 3.58%; N 14.64%. Found: C 50.66%; H 3.66%; N 14.67%.

EXAMPLE 24

3-(2-Acetamido-5-thiazolesulfonamido)-2-(2,4-dichorophenyl)-1-(1H-1,2,4-triazol-1-yl)propan-2-ol Following the procedure described in the preceeding examples but using 3-amino-2-(2,4-dichlorophenyl)-1-(1H-1,2,4-triazol-1-yl)propan-2-ol and 2-acetamido-5-thiazolesulfonylchloride, the title compound was obtained in a similar yield: mp 96°–112° C.; $^1$H NMR (80 MHz, MeOH-d$_4$)δ(TMS) 8.27 (s, 1H, CH=N), 7.74 (s, 1H, CH=N), 7.55 (d, J=8.5 Hz, 1H, arom), 7.3–7.1 (m, 2H, arom), 4.80 (AB system, Δv=0.35, J=14.5 Hz, 2H, CH$_2$-Tr), 3.74 (AB system, Δv=0.36, J=13.8Hz, 2H, CH$_2$NH), 2.37 (s, 1H, Me), 2.22 (s, 1H, Me). Anal calcd. for $C_{17}H_{18}Cl_2N_6O_4S_2$: C 40.40%; H 3.59%; N 16.63%. Found: C 40.69%; H 4.06%; N 16.70%.

EXAMPLE 25

2-(2,4-Dichlorophenyl)-3-(3-chloropropanesulfonamido-1H-1,2,4-triazol-1-yl)propan-2-ol, oxalate Following the procedure described in the preceeding examples but using 3-amino-2-(2,4-dichlorophenyl)-1-(1H-1,2,4-triazol-1-yl)propan-2-ol and 3-chloropropanesulfonylchloride, the title compound was obtained in a similar yield: mp 62°–69° C.; $^1$H NMR (80 MHz, MeOH-d$_4$)δ(TMS) 8.35 (s, 1H, CH=N), 7.79 (s, 1H, CH=N), 7.62 (d, J=8.5 Hz, 1H, arom), 7.5–7.1 (m, 2H, arom), 4.94 (AB system, Δv=0.19, J=14.5 Hz, 2H, CH$_2$-Tr), 3.84 (AB system, Δv=0.15, J=14.2 Hz, 2H, CH$_2$NH), 3.63 (t, J=6.4 Hz, 2H), 3.4–3.0 (m, 2H), 2.07 (quint, J=7, 2H). Anal calcd. for $C_{14}H_{17}Cl_3N_4O_3S$: C 37.12%; H 3.70%; N 10.82%. Found: C 37.40%; H 3.91%; N 10.87%.

EXAMPLE 26

2-(2,4-Dichlorophenyl)-3-(3-1,1-dioxotetrahydroisothiazolidin-2-yl)-1-(1H-1,2,4-triazol-1-yl)propan-2-ol Following the procedure described in example 4 but using the product obtained in the preceeding example, the title compound was obtained in a similar yield: mp 144°–145° C.; $^1$H NMR (80 MHz, MeOH-d$_4$)δ(TMS) 8.04 (s, 1H, N=CH), 7.96 (s, 1H, N=CH), 7.62 (d, J=8.5 Hz, 1H, arom), 7.4–7.1 (m, 2H, arom), 5.05 (AB system, Δv=0.62, J=14.5 Hz, 2H, CH$_2$-Tr), 3.72 (AB system, Δv=0.72, J=15.0 Hz, 2H, NCH$_2$), 3.6–2.4 (m, 4H), 2.22 (quint, J=7.2 Hz, 2H, SCH$_2$CH$_2$). Anal. calcd. for $C_{14}H_{16}Cl_2N_4O_3S$: C 42.98%; H 4.12%; N 14.32%. Found: C 43.46%; H 4.24%; N 14.23%.

EXAMPLE 27

2-(2,4-Dichlorophenyl)-3-(3-(1H-1,2,4-triazol-1-yl) propanesulfonamido]-1-(1H-1,2,4-triazol-1-yl)propan-2-ol, oxalate A solution containing 2-(2,4-dichlorophenyl)-3-(3-chloropropanesulfonamido)-1-(1H-1,2,4-triazol-1-yl)propan-2-ol and 1,2,4-triazole in dimethylformamide was heated at 50° C. for 12 h. The solution was concentrated and the product was isolated by flash chromatography to afford the title product as a white solid in low yield: mp 178°–181° C.; $^1$H NMR (80 MHz, MeOH-d$_4$)δ(TMS) 8.76 (s, 1H, CH=N), 8.43 (s, 1H, CH=N), 8.30 (s, 1H, CH=N), 7.77 (s, 1H, CH=N), 7.59 (d, J=8.5 Hz, 1H, arom), 7.5–7.1 (m, 2H, arom), 4.94 (AB system, Δv=0.42, J=14.3 Hz, 2H, CH$_2$-Tr), 4.35 (t, J=6.5 Hz, 2H, CH$_2$NH), 3.82 (AB system, Δv=0.14, J=14.0 Hz, 2H, CH$_2$NH), 3.03 (t, J=6.8 Hz, 2H, CH$_2$), 2.22 (quint; J=7, 2H).

EXAMPLE 28

2-(2,4-Dichlorophenyl)-3-(2-naphtalenesulfonamido)-1-(1-H-1,2,4-triazol-1-yl)propan-2-ol Following the procedure described in the preceeding examples but using 3-amino-2-(2,4-dichlorophenyl)-1-(1H-1,2,4-triazol-1-yl)propan-2-ol and 2-naphtalenesulfonylchloride, the title compound was obtained in a similar yield: mp 179°–180° C.; $^1$H NMR (80 MHz, CDCl$_3$)δ(TMS) 8.34 (s, 1H, arom), 8.0–7.0 (m, 11H, arom, CH=N), 5.39 (t, J=6.5 Hz, 1H, NH), 4.95 (AB system, Δv=0.55, J=14.5 Hz, 2H, CH$_2$-Tr), 3.63 (double AB system, Δv=0.30, Jd=6.5 Hz, J=13.5 Hz, 2H, NCH$_2$). Anal. calcd. for C$_{21}$H$_{18}$Cl$_2$N$_4$O$_3$S: C 52.84%; H 3.80%; N 11.74%. Found: C 52.82%; H 3.98%; N 11.42%.

EXAMPLE 29

2-(2,4-Dichlorophenyl)-3-(4-trifluoromethylbenzenesulfonamido)-1-(1H-1,2,4-triazol-1-yl)propan-2-ol Following the procedure described in the preceeding examples but using 3-amino-2-(2,4-dichlorophenyl)-1-(1H-1,2,4-triazol-1-yl)propan-2-ol and 4-trifluoromethylberLzenesulfonylchloride, the title compound was obtained in a similar yield: mp 165°–166° C.; $^1$H NMR (80 MHz, MeOH-d$_4$)δ(TMS) 8.11 (s, 1H, N=CH), 7.84 (s, 1H, N=CH), 8.0–7.0 (m, 7H, arom), 4.95 (AB system, Δv=0.43, J=14.4 Hz, 2H, CH$_2$-Tr), 3.65 (AB system, Δv=0.09, J=13.8 Hz, 2H, NCH$_2$). Anal. calcd. for C$_{18}$H$_{15}$F$_3$Cl$_2$N$_4$O$_3$S: C 43.65%; H 3.05%; N 11.13%. Found: C 43.42%; H 3.05%; N 11.13%.

EXAMPLE 30

2-(2,4-Difluorophenyl)-3-(4-trifluoromethylbenzenesulfonamido)-1-(1H-1,2,4-triazol-1-yl)propan-2-ol Following the procedure described in the preceeding examples but using 3-amino-2-(2,4-difluorophenyl)-1-(1H-1,2,4-triazol-1-yl)propan-2-ol and 4-trifluoromethylbenzenesulfonylchloride, the title compound was obtained in a similar yield: mp 161°–162° C.; $^1$H NMR (80 MHz, CDCl$_3$)δ(TMS) 8.04 (s, 1H, N=CH), 7.77 (s, 1H, N=CH), 8.0–6.5 (m, 7H, atom), 5.35 (br t, 1H, NH), 4.75 (AB system, Δv=0.098, J=14.6 Hz, 2H, CH$_2$-Tr), 3.8–3.1 (m, 2H, NCH$_2$). Anal. calcd. for C$_{18}$H$_{15}$F$_5$N$_4$O$_3$S: C 46.76%; H 3.27%; N 12.12%. Found: C 47.04%; H 3.29%; N 12.07%.

EXAMPLE 31

2-(2,4-Dichlorophenyl)-3-(N-methyl-methanelsulfonamido)-1-(1H-1,2,4-triazol-1-yl)propan-2-ol (a) 2-(2,4-Dichlorophenyl)-3-(methylamino)-1-(1H-1,2,4-triazol-1-yl)propan-2-ol A solution containing 2-(2,4-dichlorophenyl)-2-(1H-1,2,4-triazol-1-ylmethyl)oxirane (5.5 g, 20.4 mmol), obtained as explained in EP 106515, a 40% solution of methylamine in ethanol (60 mL) and ethanol is stirred at 100° C. for 16 h in a closed vessel. The product is isolated by flash chromatography as a white solid. mp 98°–101° C.; $^1$H NMR (80 MHz, CDCl$_3$)δ(TMS) 8.12 (s, 1H, N=CH), 7.81 (s, 1H, N=CH), 7.73 (d, J=8.5 Hz, 1H, arom), 7.5–7.1 (m, 2H, arom), 4.78 (s, 2H, CH$_2$-Tr), 3.28 (AB system, Δv=0.49, J=12.3 Hz, 2H, NCH$_2$), 2.29 (s, 3H, NMe).

(b) Title product

Following the procedure described in Example 1, but using the product obtained in section (a), the title product is obtained in similar yield as a solid foam. $^1$H NMR (80 MHz, MeOH-d$_4$)δ(TMS) 8.00 (s, 1H, N=CH), 7.79 (s, 1H, N=CH), 7.72 (d, J=8.5 Hz, 1H, atom), 7.4–7.1 (m, 2H, arom), 5.06 (AB system, Δv=0.59, J=14.5 Hz, 2H, CH$_2$-Tr), 3.79 (AB system, Δv=0.77, J=15.0 Hz, 2H, NCH$_2$), 2.96 (s, 3H, Me), 2.80 (s, 3H, Me). Anal. calcd. for C$_{13}$H$_{16}$Cl$_2$N$_4$O$_3$S: C 41.17%; H 4.25%; N 14.77%. Found: C 41.55%; H 4.40%; N 14.98%.

EXAMPLE 32

2-(2,4-Dichlorophenyl)-3-(N-iso-propyl-methanesulfonamido)-1-(1H-1,2,4-triazol-1-yl)propan-2-ol (a) 2-(2,4-Dichlorophenyl)-3-(iso-propylamino)-1-(1H-1,2,4-triazol-1-yl)propan-2-ol Following the procedure described in the previous example but using a solution of iso-propylamine in chloroform and heating the reaction mixture at reflux for 2 days, the corresponding amine is obtained in similar yield as a thick oil. $^1$H NMR (80 MHz, CDCl$_3$)δ(TMS) 8.31 (s, 1H, N=CH, 7.75 (s, 1H, N=CH), 7.62 (d, J=8.5 Hz, 1H, arom), 7.5–7.1 (m, 2H, arom), 4.85 (AB system, Δv=0.29, J=17.4 Hz, 2H, CH$_2$-Tr), 3.27 (AB system, Δv=0.35, J=12.7 Hz, 2H, NCH$_2$), 2.64 (m, J=6.2 Hz, 1H, CHMe$_2$), 1.98 (dd, J=1.8 Hz, J=6.2 Hz, 6H, Me$_2$).

Title product

Following the general mesylation procedure explained in example 1 but using the product obtained in the previous section, the title product is obtained in similar yield. mp 132°–133° C.; $^1$H NMR (80 MHz, CDCl$_3$)δ(TMS) 8.04 (s, 1H, N=CH), 7.79 (s, 1H, N=CH), 7.74 (d, J=8.5 Hz, 1H, atom), 7.4–7.1 (m, 2H, arom), 5.04 (AB system, Δv=0.62, J=14.4 Hz, 2H, CH$_2$-Tr), 3.79 (AB system, Δv=0.42, J=1.5 Hz, 2H, NCH$_2$), 3.78 (m, J=6.8 Hz, 1H, CHMe$_2$), 2.87 (s, 3H, MeSO$_2$), 1.23 (d, 6.8 Hz, 6H, Me$_2$). Anal. calcd. for C$_{15}$H$_{20}$Cl$_2$N$_4$O$_3$S: C 44.23%; H 4.95%; N 13.76%. Found: C 44.27%; H 5.17%; N 13.74%.

EXAMPLE 33

2-(2,4-Dichlorophenyl)-3-(N-iso-butyl-methanesulfonamido)-1-(1H-1,2,4-triazol-1-yl)propan-2-ol (a) 2-(2,4-Dichlorophenyl)-3-(iso-butylamino)-1-(1H-1,2,4-triazol-1-yl)propan-2-ol Following the procedure described in the previous example but using iso-butylamine in chloroform and heating the reaction mixture at reflux for 3 days, the corresponding amine is obtained in similar yield as a thick oil. $^1$H NMR (80 MHz, CDCl$_3$)δ(TMS) 8.14 (s, 1H, N=CH), 7.82 (s, 1H, N=CH), 7.75 (d, J=5.5 Hz, 1H, Ar), 7.4–7.1 (m, 2H, arom), 4.75 (AB system, Δv=0.15, J=14.2 Hz, 2H, CH$_2$-Tr), 3.20 (AB system, Δv=0.33, J=12.8 Hz, 2H, NCH$_2$), 2.27 (d, J=6.6 Hz, 2H, CH$_2$N), 1.59 (m, J=6.6 Hz, 1H, CHMe$_2$), 0.81 (d, J=6.6 Hz, 6H, CHMe$_2$).

(b) Title product

Following the general mesylation procedure explained in example 1 but using the product obtained in the previous section, the title product is obtained in similar yield. mp 128°–129° C.; $^1$H NMR (80 MHz, CDCl$_3$)δ(TMS) 8.03 (s, 1H, N=CH), 7.80 (s, 1H, N=CH), 7.71 (d, J=5.5 Hz, 1H, Ar), 7.4–7.1 (m, 2H, arom), 5.03 (AB system, Δv=0.66, J=14.4 Hz, 2H, CH$_2$-Tr), 3.88 (AB system, Δv=0.47, J=15.4 Hz, 2H, NCH$_2$), 3.1–2.8 (m, 2H, CH$_2$N), 2.89 (s, 3H, MeSO$_2$), 2.04 (m, J=6.6 Hz, 1H, CHMe$_2$), 0.87 (d, J=6.6 Hz, 6H, CHMe$_2$). Anal calcd. for C$_{16}$H$_{22}$Cl$_2$N$_4$O$_3$S$_2$: C 45.61%; H 5.26%; N 13.30%. Found: C 45.93%; H 5.57%; N 12.91%.

EXAMPLE 34

2-(2,4-Dichlorophenyl)-3-(N-iso-butyl-4-trifluoromethylbenzenesulfonamido)-1-(1H-1,2,4-triazol-1-yl)propan-2-ol Following the general mesylation procedure explained in example 1 but reacting 4-trifluoromethylbenzenesulfonyl chloride with the amine obtained in the previous section, the title product is obtained in similar yield as a solid foam. $^1$H NMR (80 MHz, CDCl$_3$)δ(TMS) 8.02 (s, 1H, N=CH), 7.86 (s, 1H, N=CH), 7.81 (s, 4H, Ar), 7.67 (d, J=5.5 Hz, 1H, Ar), 7.4–7.1 (m, 2H, Ar), 5.14 (AB system, Δv=0.74, J=14.5 Hz, 2H, CH$_2$-Tr), 3.77 (AB system, Δv=0.97, J=15.2 Hz, 2H, NCH$_2$), 3.2–2.8 (m, 2H, CH$_2$N), 2.05 (m, J=6.6 Hz, 1H, CHMe$_2$), 0.80 (d, 6.6 Hz, 6H, CHMe), 0.66 (d, J=6.6 Hz, 6H, CHMe). Anal calcd. for C$_{22}$H$_{23}$Cl$_2$F$_3$N$_4$O$_3$S$_2$: C 47.92%; H 4.20%; N 10.16%. Found: C 48.32%; H 4.67%; N 10.26%.

EXAMPLE 35

2-(2,4-Dichlorophenyl)-3-(N-benzyl-methanesulfonamido)-1-(1H-1,2,4-triazol-1-yl)propan-2-ol (a) 2-(2,4-Dichlorophenyl)-3-(benzylamino)-1-(1H-1,2,4-triazol-1-yl)propan-2-ol Following the procedure described in the previous example but using benzylamine in chloroform and heating the reaction mixture at reflux for 2 days, the corresponding amine is obtained in similar yield as a thick oil. $^1$H NMR (80 MHz, CDCl$_3$)δ(TMS) 8.08 (s, 1H, N=CH), 7.79 (s, 1H, N=CH), 7.71 (d, J=8.5 Hz, 1H, arom), 7.5–7.1 (m, 7H, arom), 4.78 (s, 2H, CH$_2$-Tr), 3.63 (s, 2H, CH$_2$Ph), 3.25 (AB system, Δv=0.51, J=12.8 Hz, 2H, NCH$_2$).

(b) Title product

Following the general mesylation procedure explained in example 1 but using the product obtained in the previous section, the title product is obtained in similar yield as a solid foam. $^1$NMR (80 MHz, CDCl$_3$)δ(TMS) 8.00 (s, 1H, N=CH), 7.79 (s, 1H, N=CH), 7.73 (d, J=8.5 Hz, 1H, arom), 7.4–7.1 (m, 2H, arom), 7.31 (s, 5H, Ph), 5.03 (AB system, Δv=0.62, J=14.4 Hz, 2H, CH$_2$-Tr), 4.51 (AB system, Δv=0.21, J=15.6 Hz, 2H, CH$_2$Ph), 3.89 (AB system, Δv=0.24 J=15.2 Hz, 2H, NCH$_2$), 2.64 (s, 3H, MeSO$_2$). Anal. calcd. for C$_{19}$H$_{20}$Cl$_2$N$_4$O$_3$S: C 50.12%; H 4.43%; N 12.30%. Found: C 51.25%; H 4.50%; N 11.93%.

EXAMPLE 36

3-(N-(4-Chlorobenzyl)-methanesulfonamido)-2-(2,4-dichlorophenyl)-1-(1H-1,2,4-triazol-1-yl)propan-2-ol (a) 3-(4-Chlorobenzylamino)-2-(2,4-dichlorophenyl)-1-(1H-1,2,4-triazol-1-yl) propan-2-ol Following the procedure described in the previous example but using 4-chlorobenzylamine in chloroform and heating the reaction mixture at reflux for 2 days, the corresponding amine is obtained in similar yield as a thick oil. $^1$H NMR (80 MHz, CDCl$_3$)δ(TMS) 8.08 (s, 1H, N=H), 7.79 (s, 1H, N=H), 7.71 (d, J=8.5 Hz, 1H, arom), 7.5–7.1 (m, 7H, arom), 4.78 (s, 2H, CH$_2$-Tr), 3.63 (s, 2H, CH$_2$Ph), 3.25 (AB system, Δv=0.51, J=12.8 Hz, 2H, NCH$_2$).

(b) Title product

Following the general mesylation procedure explained in example 1 but using the product obtained in the previous section, the title product is obtained in similar yield. mp 121°–122° C.; $^1$H NMR (80 MHz, CDCl$_3$)δ(TMS) 8.09 (s, 1H, N=CH), 7.82 (s, 1H, N=CH), 7.69 (d, J=8.5 Hz, 1H, arom), 7.4–7.1 (m, 6H, arom), 5.02 (AB system, Δv=0.65, J=14.4 Hz, 2H, CH$_2$-Tr), 4.46 (AB system, Δv=0.19, J=15.5 Hz, 2H, CH$_2$Ph), 3.86 (AB system, Δv=0.27, J=15.4 Hz, 2H, NCH$_2$), 2.69 (s, 3H, MeSO$_2$). Anal. calcd. for C$_{19}$H$_{19}$Cl$_3$N$_4$O$_3$S: C 46.59%; H 3.91%; N 11.44%. Found: C 47.39%; H 4.40%; N 11.05%.

EXAMPLE 37

2-(2,4-Dichlorophenyl)-3-(N-(4-trifluromethylbenzyl)-methanesulfonamido)-1-(1H-1,2,4-triazol-1-yl)propan-2-ol (a) 2-(2,4-Dichlorophenyl)-3-(4-trifluoromethylbenzylamino)1-(1H-1,2,4-triazol-1-yl)propan-2-ol Following the procedure described in the previous example but using 4-trifluoromethylbenzylamine in chloroform and heating the reaction mixture at reflux for 2 days, the corresponding amine is obtained in similar yield as a paste. $^1$H NMR (80 MHz, CDCl$_3$)δ(TMS) 8.07 (s, 1H, N=CH), 7.81(s, 1H, N=CH), 7.8–7.0 (m, 7H, arom), 4.82 (s, 2H, CH$_2$-Tr), 3.73 (s, 2H, CH$_2$Ph), 3.26 (AB system, Δv=0.41, J=12.5 Hz, 2H, NCH$_2$)

(b) Title product

Following the general mesylation procedure explained in example 1 but using the product obtained in the previous section, the title product is obtained in similar yield. mp 139°–141° C.; $^1$H NMR (80 MHz, CDCl$_3$)δ(TMS) 8.07 (s, 1H, N=CH, 7.82 (s, 1H, N=CH), 7.8–7.0 (m, 7H, arom), 5.02 (AB system, Δv=0.66, J=14.4 Hz, 2H, CH$_2$-Tr), 4.55 (AB system, Δv=0.16, J=15.7 Hz, 2H, CH$_2$Ph), 3.85 (AB system, Δv=0.41, J=15.5 Hz, 2H, NCH$_2$), 2.75 (s, 3H, MeSO$_2$). Anal. calcd. for C$_{20}$H$_{19}$Cl$_2$F$_3$N$_4$O$_3$S; C 45.90%; H 3.66%; N 10.71%. Found: C 6.34%; H 3.95%; N 10.38%.

EXAMPLE 38

2-(2,4-Dichlorophenyl)-3-(N-(4-fluoromethylbenzyl)-methanesulfonamido)-1-(1H-1,2,4-triazol-1-yl)propan-2-ol (a) 2-(2,4-Dichlorophenyl)-3-(4-fluoromethylbenzylamino)-1-(1H-1,2,4-triazol-1-yl)propan-2-ol Following the procedure described in the previous example but using 4-fluoromethylbenzylamine in chloroform and heating the reaction mixture at reflux for 2 days, the corresponding amine is obtained in similar yield as a paste. $^1$H NMR (80 MHz, CDCl$_3$)δ(TMS) 8.07 (s, 1H, N=CH), 7.96 (s, 1H, N=CH), 7.70 (d, J=8.5 Hz, 1H, arom), 7.5–6.9 (m, 6H, arom), 4.79 (s, 2H, CH$_2$-Tr), 3.62 (s 2H, NCH$_2$), 3.24 (AB system, Δv=0.46, J=12.7 Hz, 2H, NCH$_2$).

(b) Title product

Following the general mesylation procedure explained in example 1 but using the product obtained in the previous section, the title product is obtained in similar yield as a solid foam. $^1$H NMR (80 MHz, CDCl$_3$)δ(TMS) 8.05 (s, 1H, N=CH), 7.86 (s, 1H, N=CH, 7.71 (d, J=8.5 Hz, 1H, arom), 7.5–6.9 (m, 6H, arom), 5.02 (AB system, Δv=0.66, J=14.4 Hz, 2H, CH$_2$-Tr), 4.47 (AB system, Δv=0.21, J=15.2 Hz, 2H, CH$_2$Ar), 3.85 (AB system, Δv=0.41, J=15.5 Hz, 2H, NCH$_2$), 2.68 (s, 3H, MeSO$_2$). Anal. calcd. for C$_{19}$H$_{19}$Cl$_2$FN$_4$O$_3$S: C 48.21%; H 4.05%; N 11.84%. Found: C 47.83%; H 4.34%; N 11.91 %.

EXAMPLE 39

2-(2,4-Dichlorophenyl)-3-(N-(2-phenylethyl)-methanesulfonamido)1-(1H-1,2,4-triazol-1-yl)propan-2-ol (a) 2-(2,4-Dichlorophenyl)-3-(2-phenylethylamino)-1-(1H-1,2,4-triazol-1-yl)propan-2-ol Following the procedure described in the previous example but using 2-phenylethylamine in chloroform and heating the reaction mixture at reflux for 2 days, the corresponding amine is obtained in similar yield as a thick oil. $^1$H NMR (80 MHz, CDCl$_3$)δ(TMS) 8.10 (s, 1H, N=CH), 7.67(s, 1H, N=CH), (d, J=8.5 Hz, 1H, arom), 7.5–7.1 (m, 7H, arom), 4.72 (AB system, Δv=0.13, J=14.2 Hz, 2H, CH$_2$-Tr), 3.21 (AB system, Δv=0.40, J=12.8 Hz, 2H, NCH$_2$), 2.7–2.5 (m, 4H, CH$_2$CH$_2$Ph).

(b) Title product

Following the general mesylation procedure explained in example 1 but using the product obtained in the previous section, the title product is obtained in similar yield. mp 138°–140° C.; $^1$H NMR (80 MHz, CDCl$_3$)δ(TMS) 8.03 (s, 1H, N=CH), 7.80(s, 1H, N=CH), 7.75 (d, J=8.5 Hz, 1H, arom), 7.4–7.1 (m, 7H, arom), 5.04 (AB system, Δv=0.62, J=14.4 Hz, 2H, CH$_2$-Tr), 3.88 (AB system, Δ=0.46, J=15.2 Hz, 2H, NCH$_2$), 3.6–3.3 (m, 2H, CH$_2$), 3.1–2.7 (m, 2H, CH$_2$), 2.69 (s, 3H, MeSO$_2$). Anal. calcd. for C$_{20}$H$_{22}$Cl$_2$N$_4$O$_3$S: C 51.18%; H 4.72%; N 11.94%. Found: C 51.27%; H 4.97%; N 11.84%.

EXAMPLE 40

2-(2,4-Dichlorophenyl)-3-(N-(2-pyridylmethyl)-methanesulfonamido)1-(1H-1,2,4-triazol-1-yl)propan-2-ol (a) 2-(2,4-Dichlorophenyl)-3-(2-pyridylmethylamino)-1-(1H-1,2,4-triazol-1-yl)propan-2-ol Following the procedure described in the previous example but using 2-pyridylmethylamine in chloroform and heating the reaction mixture at reflux for 2 days, the corresponding amine is obtained in similar yield as a thick oil. $^1$H NMR (80 MHz, CDCl$_3$)δ(TMS) 8.6–8.4 (br d, 1H, pyr), 8.13 (s, 1H, N=CH), 7.78 (s, 1H, N=CH, 7.77 (d, 8.5 Hz, 1H, arom), 7.8–7.1 (m, 5H, arom, pyr), 4.79 (s, 2H, CH$_2$-Tr), 3.77 (s, 2H, CH$_2$-pyr), 3.30 (AB system, Δv=0.69, J=11.3 Hz, 2H, NCH$_2$).

(b) Title product

Following the general mesylation procedure explained in example 1 but using the product obtained in the previous section, the title product is obtained in similar yield. mp 154°–156° C.; $^1$H NMR (80 MHz, CDCl$_3$)δ(TMS) 8.63 (br d, 1H, pyr), 8.00 (s, 1H, N=CH, 7.80 (s, 1H, N=CH), 7.78 (d, J=8.5 Hz, 1H, arom), 7.8–7.6 (m, 1H, pyr), 7.4–7.1 (m, 4H, atom, pyr), 5.06 (AB system, Δv=0.46, J=14.4 Hz, 2H, CH$_2$-Tr), 4.60 (s, 2H, CH$_2$-pyr), 4.067 (AB system, Δv=0.44, J=15.2 Hz, 2H, NCH$_2$), 2.72 (s, 3H, MeSO$_2$) Anal. calcd. for C$_{18}$H$_{19}$Cl$_2$N$_5$O$_3$S: C 47.38%; H 4.20%; N 15.35%. Found: C 47.52%; H 4.19%; N 15.65%.

EXAMPLE 41

2-(2,4-Dichlorophenyl)-3-(N-(2-(2-pyridyl)ethyl)-methanesulfonamido)1-(1H-1,2,4-triazol-1-yl)propan-2-ol (a) 2-(2,4-Dichlorophenyl)-3-((2-(2-pyridyl)ethyl)amino)-1-(1H-1,2,4-triazol-1-yl)propan-2-ol Following the procedure described in the previous example but using 2-(2-pyridyl)ethylamine in chloroform and heating the reaction mixture at reflux for 2 days, the corresponding amine is obtained in similar yield as a thick oil. $^1$NMR (80 MHz, CDCl$_3$)δ(TMS) 8.46 (br d, 1H, pyr), 8.13 (s, 1H, N=CH), 7.77 (s, 1H, N=H), 7.71 (d, J=8.5 Hz, 1H, arom), 7.4–6.9 (m, 5H, arom, pyr), 4.74 (AB system, Δv=0.09, J=14.3 Hz, 2H, CH$_2$-Tr), 3.29 (AB system, Δv=0.49, J=12.5 Hz, 2H, NCH$_2$), 2.88 (s, 4H, CH$_2$CH$_2$-pyr).

(b) Title product

Following the general mesylation procedure explained in example 1 but using the product obtained in the previous section, the title product is obtained in similar yield.

mp 151°–153° C.; $^1$H NMR (80 MHz, CDCl$_3$)δ(TMS) 8.58 (br d, 1H, pyr), 7.95 (s, 1H, N=CH), 7.78 (s, 1H, N=CH), 7.73 (d, J=8.5 Hz, 1H, arom), 7.8–7.6 (m, 1H, pyr), 7.4–7.1 (m, 4H, arom, pyr), 5.05 (AB system, Δv=0.71, J=14.5 Hz, 2H, CH$_2$-Tr), 3.90 (AB system, Δv=0.78, J=15.1 Hz, 2H, NCH$_2$), 3.9–3.5 (m, 2H, CH$_2$), 3.5–3.1 (m, 2H, CH$_2$), 2.72 (s, 3H, MeSO$_2$). Anal. calcd. for C$_{19}$H$_{21}$Cl$_2$N$_5$O$_3$S: C 48.52%; H 4.50%; N 14.89%. Found: C 48.55%; H 4.73%; N 14.64%.

EXAMPLE 42

2-(2,4-Dichlorophenyl)-3-(N-(2-furanylmethyl)-methanesulfonamido)-1-(1H-1,2,4-triazol-1-yl)propan-2-ol (a) 2-(2,4-Dichlorophenyl)-3-(2-furanylmethylamino)-1-(1H-1,2,4-triazol-1-yl)propan-2-ol Following the procedure described in the previous example but using 2-furanylmethylamine in chloroform and heating the reaction mixture at reflux for 2 days, the corresponding amine is obtained in similar yield as a thick oil. $^1$H NMR (80 MHz, CDCl$_3$)δ(TMS) 8.09 (s, 1H, N=CH), 7.80 (s, 1H, N=CH), 7.71 (d, J=8-Hz, 1H, atom), 7.4–7.1 (m, 3H, arom, fur), 6.27 (t, J=1.7 Hz, 1H, fur), 6.08 (d, J=3.0 Hz, 1H, fur), 4.79 (s, 2H, CH$_2$-Tr), 3.64 (s, 2H, CH$_2$-fur), 3.24 (AB system, Δv=0.52, J=12.8 Hz, 2H, NCH$_2$).

(b) Title product

Following the general mesylation procedure explained in example 1 but using the product obtained in the previous section, the title product is obtained in similar yield. mp 114°–115° C.; ¹H NMR (80 Hz, CDCl₃)δ(TMS) 8.04 (s, 1H, N=CH), 7.81 (s, 1H, N=CH), 7.73 (d, J=8.5 Hz, 1H, arom), 7.5–7.1 (m, 3H, arom, fur), 6.36 (s, 2H, fur), 5.13 (AB system, Δv=0.66, J=14.5 Hz, 2H, CH₂-Tr), 4.63 (AB system, Δv=0.20, J=16.4 Hz, 2H, CH₂-fur), 3.80 (AB system, Δv=0.45, J=15.2 Hz, 2H, NCH₂), 2.72 (s, 3H, MeSO₂). Anal. calcd. for C₁₇H₁₈Cl₂N₄O₄S: C 45.85%; H 4.07%; N 12.58%. Found: C 45.48%; H 4.32%; N 12.29%.

EXAMPLE 43

3-(N-(Cyclohexylmethyl)-methanesulfonamido)-2-(2,4-dichlorophenyl)-1-(1H-1,2,4-triazol-1-yl)propan-2-ol (a) 2-(2,4-Dichlorophenyl)-3-(cyclohexylmethylamino)-1-(1H-1,2,4-triazol-1-yl)propan-2-ol Following the procedure described in the previous example but using cyclohexylmethylamine in chloroform and heating the reaction mixture at reflux for 2 days, the corresponding amine is obtained in similar yield as a paste. ¹H NMR (80 MHz, CDCl₃)δ(TMS) 8.14 (s, 1H, N=CH), 7.81 (s, 1H, N=CH), 7.75 (d, J=8.5 Hz, 1H, arom), 4.74 (AB system, Δv=0.13, J=13.5 Hz, CH₂-Tr), 3.20 (AB system, Δv=0.37, J=12.7 Hz, 2H, NCH₂), 2.27 (d, J=5.8 Hz, 2H, CH₂-chx), 2.0–0.6 (m, 11H, chx).

(b) Title product

Following the general mesylation procedure explained in example 1 but using the product obtained in the previous section, the title product is obtained in similar yield. mp 168°–169° C.; ¹H NMR (80 MHz, CDCl₃)δ(TMS) 8.03 (s, 1H, N=CH), 7.79 (s, 1H, N=CH), 7.73 (d, J=8.5 Hz, 1H, arom), 7.4–7.1 (m, 2H, arom), 4.99 (AB system, Δv=0.56, J=14.5 Hz, 2H, CH₂-Tr), 3.88 (AB system, Δv=0.35, J=15.4 Hz, 2H, NCH₂), 3.1–2.8 (m, 2H, CH₂-chx), 2.87 (s, 3H, MeSO₂), 2.0–0.7 (m, 11H, chx). Anal. calcd. for C₁₉H₂₆Cl₂N₄O₃S: C 49.46%; H 5.68%; N 12.40%. Found: C 49.34%; H 5.90%; N 12.14%.

EXAMPLE 44

(2R*,3R*)-2-(2,4-Dichlorophenyl)-3-methanesulfonamido-1-(1H-1,2,4-triazol-1-yl)butan-2-ol Following the general mesylation procedure explained in example 1 and using (2R*,3R*)-3-amino-2-(2,4-dichlorophenyl)-1-(1H-1,2,4-triazol-1-yl)butan-2-ol, prepared as described in EP 332,387, the title product is obtained in similar yield. mp 177°–180° C.; ¹H NMR (80 MHz, MeOH-d₄)δ(TMS) 8.01 and 7.93 (s, 1H, N=CH), 7.74 (s, 1H, N=CH), 7.6–7.0 (m, atom), 5.58 and 5.52 (d, J=14.7 Hz, 1H, CH(H)-Tr), 5.0–4.5 (m, 2H, NCHMe, CH(H)-Tr), 3.06 (s, 3H, MeSO₂), 1.00 (d, J=6.8 Hz, 3H, MeCH). MS (CI, NH₃) 379 (M+1) Anal. calcd. for C₁₃H₁₆Cl₂N₄O₃S: C 41.17%; H 4.25%; N 14.77%. Found: C 41.30%; H 4.51%; N 14.76%.

EXAMPLE 45

(2R*,3R*)-3-(4-Chlorobenzenesulfonamido)-2-(2,4-dichlorophenyl)-1-(1H-1,2,4-triazol-1-yl)butan-2-ol Following the general sulfonylation procedure explained in example 1 and using (2R*,3R*)-3-amino-2-(2,4-dichlorophenyl)-1-(1H-1,2,4-triazol-1-yl)butan-2-ol, prepared as described in EP 332,387, and 4-chlorobenzenesulfonyl chloride, the title product is obtained in similar yield. mp 160°–165° C.; ¹H NMR (80 MHz, CDCl₃)δ(TMS) 7.92 (s, 1H, N=CH, 7.81 (s, arom), 7.6–6.9 (m, arom), 5.10 (AB system, Δv=0.72, J=14.5 Hz, CH₂-Tr), 5.8 (d, J=10 Hz, 1H, NH), 4.7–4.4 (m, 1H, CHMe), 0.62 (d, J=6.5 Hz, 3H, MeCH). MS (CI, NH₃) 475 (M+1) Anal. calcd. for C₁₈H₁₇Cl₃N₄O₃S: C 45.44%; H 3.60%; N 11.78%. Found: C 45.53%; H 4.10%; N 12.27%.

EXAMPLE 46

5-(2,4-Dichlorophenyl)-3-methanesulfonyl-5-[(1H-1,2,4-triazol-1-yl]methyl)oxazolidine Following the general mesylation procedure explained in example 1 but using 5-(2,4-dichlorophenyl)-5-[(1H-1,2,4-triazol-1-yl]methyl) oxazolidine, obtained according to Konosu et al, Chem. Pharm. Bull., 38 (9), 2476, 1990, the title product is obtained in similar yield. mp 144°–145° C. ¹H NMR (80 MHz, CDCl₃)δ(TMS) 8.04 (s, 1H, N=CH), 7.76 (s, 1H, N=CH), 7.5–7.1 (m, 3H, arom), 4.98 (AB system, Δv=0.13, J=6.5 Hz, 2H, NCH₂O), 4.81 (s, 2H, CH₂-Tr), 4.12 (AB system, Δv=0.26, J=15.2 Hz, 2H, NCH₂), 2.79 (s, 3H, MeSO₂). Anal. calcd. for C₁₃H₁₄Cl₂N₄O₃S: C 41.39%; H 3.74%; N 14.85%. Found: C 41.12%; H 3.88%; N 14.57%.

EXAMPLE 47

5-(2,4-Dichlorophenyl)-3-(4-trifluoromethylbenzenesulfonyl)-5-[(1H-1,2,4-triazol-1-yl] methyl)oxazolidine Following the general sulfonylation procedure explained in example 1 but using 5-(2,4-dichlorophenyl)-5-[(1H-1,2,4-triazol-1-yl]methyl) oxazolidine, obtained according to Konosu et al, Chem. Pharm. Bull., 38 (9), 2476, 1990, and 4-trifluoromethylbenzene-sulfonyl chloride, the title product is obtained in similar yield. mp 160°–162° C.; ¹H NMR (80 MHz, CDCl₃)δ(TMS) 7.93 (s, 1H, N=CH), 7.78 (s, 1H, N=CH), 7.9–7.2 (m, 5H, arom), 6.91 (s, 2H, arom), 5.00 (s, 2H, NCH₂O), 4.62 (s, 2H, CH₂-Tr), 4.11 (s, 2H, NCH₂). Anal. calcd. for C₁₉H₁₅F₃Cl₂N₄O₃S: C 44.98%; H 2.98%; N 11.04%. Found: C 44.80%; H 2.88%; N 11.37%.

EXAMPLE 48

5-(2,4-Dichlorophenyl)-3-methanesulfonyl-2-methyl-5-[(1,2,4-triazol-1-yl]methyl)oxazolidine, oxalate Following the general mesylation procedure explained in example 1 but using 5-(2,4-dichlorophenyl)-2-methyl-5-([1H-1,2,4-triazol-1-yl]methyl)oxazolidine, obtained according to patent ES 334509/91, the title product is obtained in a similar yield after oxalate formation. The NMR analysis indicates only one isomer. mp 155°–158 ° C. ¹H NMR (80 MHz, CDCl₃)δ(TMS) 8.22 (s, 1H, N=CH), 7.91 (s, 1H, N=CH), 7.6–7.2 (m, 3H, arom), 5.27 (q, J=5.5 Hz, 1H CHMe), 4.74 (AB system, Δv=0.32, J=14.6 Hz, 2H, CH₂-Tr), 4.13 (AB system, Δv=0.50, J=10.4 Hz, 2H, NCH₂), 2.49 (s, 3H, MeSO₂), 1.42 (d, J=5.5 Hz, 3H, MeCH). Anal. calcd. for C₁₄H₁₆Cl₂N₄O₃·½(CO₂H)₂: C 41.30%; H 3.93%; N 12.84%. Found: C 41.16%; H 4.10%; N 12.58%.

EXAMPLE 49

5-(2,4-Dichlorophenyl)-2-methyl-3-(4-trifluoromethylbenzenesulfonyl)-5-[(1H-1,2,4-triazol-1-yl]methyl)oxazolidine Following the general sulfonylation procedure explained in example 1 but using 5-(2,4-dichlorophenyl)-2-methyl-5-[(1H-1,2,4-triazol-1-yl]methyl)oxazolidine, obtained according to patent ES 334509/91 and 4-trifluoromethylbenzenesulfonyl chloride, the title product is obtained in similar yield as a single isomer. mp 188°–190° C. $^1$H NMR (80 MHz, CDCl$_3$)δ(TMS) 8.06 (s, 1H, N=CH), 7.80 (s, 1H, N=CH), 7.7–7.2 (m, 5H, arom), 7.02 (s, 2H, arom), 5.20 (q, J=5.3 Hz, 1H, CHMe), 4.60 (AB system, Δν=0.32, J=14.6 Hz, 2H, CH$_2$-Tr), 4.13 (AB system, Δν=0.62, J=12 Hz, 2H, NCH$_2$), 1.49 (d, J=5.3 Hz, 3H, CHMe). Anal. calcd. for C$_{20}$H$_{17}$F$_3$Cl$_2$N$_4$O$_3$S: C 46.08%; H 3.29%; N 10.75%. Found: C 46.34%; H 3.54%; N 10.43%.

EXAMPLE 50

2-(4-Chlorophenyl)-5-(2,4-dichlorophenyl)-3-methanesulfonyl-5-[(1H-1,2,4-triazol-1-yl]methyl)oxazolidine Following the general mesylation procedure explained in example 1 but using 2-(4-chlorophenyl)-5-(2,4-dichlorophenyl)-5-[(1H-1,2,4-triazol-1-yl] methyl-)oxazolidine, obtained according to patent ES 334509/91, the title product is obtained in a similar yield.

EXAMPLE 51

(4R*-5R*)-5-(2,4-Dichlorophenyl)-3-methanesulfonyl-4-methyl-5-[(1H-1,2,4-triazol-1-yl]methyl)oxazolidine Following the general mesylation procedure explained in example 1 but using (4R*,5R*)-5-(2,4-dichlorophenyl)-4-methyl-5-[(1H-1,2,4-triazol-1-yl]methyl)oxazolidine, obtained according to EP 332,387, the title product is obtained in a similar yield. mp 167°–172° C.; $^1$H NMR (80 MHz, CDCl$_3$)δ(TMS) 7.77 (s), 1H, N=CH), 7.66 (s), 7.5–7.0 (m, arom), 5.52 (d, J=4 Hz, 1H), 5.2–4.5 (m, 4H), 3.08 (s, 3H, MeSO$_2$), 1.04 (d, J=6.8 Hz, 3H, MeCH). Anal. calcd. for C$_{14}$H$_{16}$Cl$_2$N$_4$O$_3$S.1/6hexane: C 44.45%; H 4.48%; N 13.82%. Found: C 44.75%; H 4.78%; N 14.06%.

EXAMPLE 52

(4R*-5R*)-5-(2,4-Dichlorophenyl)-2,4-dimethyl-3-methanesulfonyl-5-[(1H-1,2,4-triazol-1-yl]methyl)oxazolidine Following the general mesylation procedure explained in example 1 but using (4R*,5R*)-5-(2,4-dichlorophenyl)-2,4-dimethyl-5-[(1H-1,2,4-triazol-1-yl]methyl)oxazolidine, obtained according to ES 334509/91, the title product is obtained in a low yield as a solid. mp 160°–170° C.; $^1$H NMR (80 MHz, CDCl$_3$)δ(TMS) 7.66 (br s, 2H, triazole), 7.5–7.0 (m, 3H, arom), 5.77 (q, J=5.1 Hz, 1H, OCHMe), 5.7–4.6 (m, 3H, CH$_2$Tr, CHMe), 3.08 and 3.05 (s, 3H, MeSO$_2$), 1.83 and 1.62 (d, J=5.1 Hz, 3H, OCHMe), 1.21 and 1.04 (d, J=6.5 Hz, 3H, MeCH. MS (CI, CH$_4$): 405 (M+1). Anal. calcd. for C$_{15}$H$_{17}$Cl$_2$N$_4$O$_3$S: C 44.56%; H 4.24%; N 13.86%. Found: 44.56%; H 4.24%; N 13.86%

EXAMPLE 53

In vitro testing

The in vitro evaluation was carried out by the agar dilution method using Kimmig's agar (K.A., E.Merck, Darmstadt, Germany) supplemented with 0.5% glycerol. Sterile 18 mL blanks of KA and serial dilutions in Kimmig's broth (800 to 0.25 mg/mL) of the test drugs are prepared. A 2 mL aliquote of each drug dilution is added to a 18 ml K.A. blank. The 20 mL volumes of drugs in agar are mixed and poured into sterile Petri dishes and allowed to harden. Two drug free plates of K.A. are prepared in a similar way with 2 mL of sterile purified water and 2 mL of ethanol 50%, respectively. Drug containing plates as well as the two drug free plates for each experiment are inoculated with 10 mL of the fungal inocula. One drug-free plate is inoculated at the beginning and one at the end of each individual series of plate inoculations. All test organisms are incubated at 30° C. The incubation time is 48 h for yeasts and 120 h for dermatophytes and moulds. Following incubation, the test plates are examinated to determine individual mimimal inhibitory concentrations (MIC) defined as the lowest concentration of drug preventing macroscopically visible growth.

EXAMPLE 54

In vivo testing

The in vivo evaluation was carried out by i.v. inoculation of a group of 10 mice with 0.2 mL of a suspension containing 2 to 5×10$^6$ ucf/mL of *Candida albicans* per mouse. Mice received an oral dose of 20 mg/kg of the compound of formula I at times 1, 4 and 24 h post infection. All untreated animals died between days 3 to 5. The antifungal activity was assessed by the survival rate 9 days after infection.

What is claimed is:

1. A compound of formula Ia:

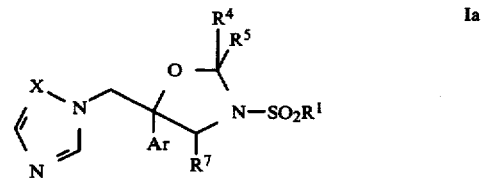

in which:

X is N or CH;

R$^1$ is C$_1$–C$_6$ alkyl, C$_1$–C$_4$ haloalkyl, C$_3$–C$_6$ cycloalkyl, phenyl-C$_1$–C$_4$-alkyl, a phenyl-C$_1$–C$_4$-alkyl group where the phenyl ring carries a substituent selected from the group consisting of (a) as specified below, phenyl, naphthyl, a phenyl ring substituted with one or more members of group (a), quinolyl, or isoquinolyl,;

R$_4$ is hydrogen, C$_1$–C$_6$ alkyl, or (1H-1,2,4-triazol-1-yl)methyl;

R$^5$ is hydrogen, C$_1$–C$_6$ alkyl, phenyl or a phenyl group substituted with a member of group (a)

R$^7$ is hydrogen or C$_1$–C$_6$ alkyl;

Ar is phenyl or a phenyl ring substituted with one or more halogen or trifluoromethyl groups;

wherein group (a) consists of: C$_1$–C$_4$ alkyl, C$_1$–C$_4$ haloalkyl, C$_1$–C$_4$ alkoxy, C$_1$–C$_4$ haloalkoxy, halogen, CF$_3$, NO$_2$, CN, OH, OCH$_2$Ph, CH$_2$OH, NHAc, a group of formula —CH$_2$—OCO—R$^6$, a group of formula —CO—R$^6$, a group of formula —COO— R$^6$, a group of formula —SO$_2$R$^6$, NH$_2$, NHR$^6$, or NR$^6{}_2$;

R$^6$ is C$_1$–C$_4$ alkyl;

Z is 0, 1 or 2;

or an acid-addition salt thereof.

2. A compound according to claim 1 of formula Ia, in which:

X is N;

Ar is a phenyl ring substituted with one or two chlorine, fluorine or trifluoromethyl groups, or a combination thereof;

R$^4$ and R$^5$ are both hydrogen, or R$^4$ is hydrogen and R$^5$ is C$_1$–C$_6$ alkyl or phenyl.

3. A compound according to claim 1 or 2 wherein R$^1$ is methyl, ethyl, or propyl.

4. 5-(2,4-Dichlorophenyl)-3-methanesulfonyl-5-([1H-1,2,4-triazol-1-yl]methyl)oxazolidine.

5. (4R*,5R*)-5-(2,4-Dichlorophenyl)-3-methanesulfonyl-4-methyl-5-([1H-1,2,4-triazol-1-yl]methyl)oxazolidine.

6. (4R*,5R*)-5-(2,4-Difluorophenyl)-3-methanesulfonyl-4-methyl-5-([1H-1,2,4-triazol-1-yl]methyl)oxazolidine.

7. A pharmaceutical composition comprising a pharmaceutically acceptable carrier or diluent in admixture with an antifungal effective amount of a compound of claim 1.

8. An agrochemical composition comprising an agronomically acceptable carrier or diluent in admixture with an antigungal effective amount of a compound of claim 1.

9. A method for treating fungal infections in an animal, which comprises administering to an animal in need thereof an antifungal-effective amount of a compound of claim 1.

10. A method according to claim 9 wherein the administration step comprises oral or parental administration and the antifungal-effective amount is from 0.010 to 20 mg/kg of body weight.

11. A method of con, batting fungal diseases in a plant, which comprises applying to the plant, to the seed of the plant or to the locus of the plant or an antifungal effective amount of seed a compound of claim 1.

* * * * *

UNITED STATES PATENT AND TRADEMARK OFFICE
CERTIFICATE OF CORRECTION

PATENT NO. : 5,344,839

DATED : September 6, 1994

INVENTOR(S) : Javier Bartroli et al.

It is certified that error appears in the above-indentified patent and that said Letters Patent is hereby corrected as shown below:

Col. 1, line 56, "$C_1C_6$" should be -- $C_1$-$C_6$ --; Col. 2, line 6, "(a)below" should be -- (a) below --; Col. 2, line 17, "pyridyl-$C_1$-$C_4$alkyl" should be -- pyridyl-$C_1$-$C_4$ alkyl --;

Col. 3, line 55, "cydobutyl, cydopentyl or cydohexyl" should be -- cyclobutyl, cyclopentyl or cyclohexyl --; Col. 6, line 19, "4-chlorphenyl" should be -- 4-chlorophenyl --; Col. 9, line 26, "47 and" should be -- 47, --; Col. 9, line 46, "5-(LIH-1,2,3-triazol" should be -- 5-([1H-1,2,4-triazol --; Col. 10, line 24, "rain" should be -- min --; Col. 12, line 3, "*flayus*" should be -- *flavus* --; Col. 12, line 4, "*furnigatus*" should be -- *fumigatus* --; Col. 12, line 4, "*Histoplasrna*" should be -- *Histoplasma* --; Col. 12, line 5, "*Blastornyces*" should be -- *Blastomyces* --; Col. 12, line 64, "atom" should be -- arom --; Col. 13, line 47, "atom" should be -- arom --; Col. 13, line 59, "add" should be -- acid --; Col. 14, line 12, "atom" should be -- arom --; Col. 14, line 49, "Chlorobenzenesulfonarnido" should be -- Chlorobenzenesulfonamido --; Col. 14, line 50, "phenYl)" should be -- phenyl) --; Col. 14, line 55, after "N=CH" insert -- ) --; Col. 16, line 65, "atom" should be -- arom --; Col. 16, line 67, after "CH$_2$NH" insert -- ), --; Col. 17, line 15, after "(m, 1H, NH" insert -- ) --; Col. 19, line 18, "J=6.5" should be -- J=6.8 --; Col. 19, line 45, "thylberLzene-sulfonylchloride" should be — thylbenzenesulfonylchloride—; Col. 19, line 64, "atom" should be -- arom --; Col. 20, line 24, "atom" should be -- arom --; Col. 20, line 41, after "N=CH" (first occurrence) insert -- ) --; Col. 20, line 53, "atom" should be -- arom --;

UNITED STATES PATENT AND TRADEMARK OFFICE
CERTIFICATE OF CORRECTION

PATENT NO. : 5,344,839

DATED : September 6, 1994

INVENTOR(S) : Javier Bartroli et al.

It is certified that error appears in the above-indentified patent and that said Letters Patent is hereby corrected as shown below:

Col. 20, line 55, "J=1.5 Hz" should be -- J=15.5 Hz --; Col. 22, line 15, "N=H" (both occurrences) should be -- N=CH --; Col. 22, line 53, after "N=CH" insert -- ) --; Col. 22, line 59, "6.34%" should be -- 46.34% --; Col. 23, line 16, after "N=CH" insert -- ) --; Col. 23, line 36, before "(d, J=8.5" insert -- 7.68 --; Col. 23, line 68, after "N=CH" insert -- ) --; Col. 24, line 9, after "N=CH" (first occurrence) insert -- ) --; Col. 24, line 10, "atom" should be -- arom --; Col. 24, line 29, "N=H" should be -- N=CH --; Col. 24, line 31, "J=12.5 Hz" should be -- J=12.8 Hz --; Col. 24, line 60, "J=8-Hz" should be -- J=8.5 Hz --; Col. 24, line 61, "atom" should be -- arom --; Col. 25, line 1, "80 Hz" should be -- 80 MHz --; Col. 25, line 50, "atom" should be -- arom --; Col. 25, line 64, "chlorobertzenesulfonyl" should be -- chlorobenzenesulfonyl --; Col. 25, line 66, after "N=CH" insert -- ) --; Col. 26, line 1, "J=6.5 Hz" should be -- J=6.8 Hz --; Col. 26, line 42, "[(1,2,4" should be -- [(1H-1,2,4 --; Col. 27, line 51, "J=6.5 Hz" should be -- J=6.8 Hz --; Col. 27, line 51, after "MeCH" insert -- ) --;

In the Claims: Col. 29, line 12 (claim 7), after "antifungal" insert a dash; Col. 30, line 1 (claim 8), "antigungal effective" should be -- antifungal-effective --;

UNITED STATES PATENT AND TRADEMARK OFFICE
CERTIFICATE OF CORRECTION

PATENT NO.   : 5,344,839
DATED        : September 6, 1994
INVENTOR(S)  : Javier Bartroli et al.

It is certified that error appears in the above-indentified patent and that said Letters Patent is hereby corrected as shown below:

Col. 30, claim 11 should read -- A method of combatting fungal diseases in a plant, which comprises applying to the plant, to the seed of the plant or to the locus of the plant or seed an antifungal-effective amount of a compound of claim 1. --.

Signed and Sealed this

Sixteenth Day of May, 1995

Attest:

BRUCE LEHMAN

Attesting Officer

Commissioner of Patents and Trademarks